United States Patent
Kalhor et al.

(10) Patent No.: US 10,851,369 B2
(45) Date of Patent: Dec. 1, 2020

(54) FREQUENCY-BASED MODULATION OF DIVERSE SPECIES IN A NUCLEIC ACID LIBRARY

(71) Applicant: President and Fellows of Harvard College, Cambridge, MA (US)

(72) Inventors: Reza Kalhor, East Boston, MA (US); Javier Fernandez Juarez, Cambridge, MA (US); Henry Hung-yi Lee, Brookline, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/310,643

(22) PCT Filed: Jun. 21, 2017

(86) PCT No.: PCT/US2017/038414
§ 371 (c)(1),
(2) Date: Dec. 17, 2018

(87) PCT Pub. No.: WO2017/223127
PCT Pub. Date: Dec. 28, 2017

(65) Prior Publication Data
US 2019/0177720 A1    Jun. 13, 2019

Related U.S. Application Data

(60) Provisional application No. 62/352,768, filed on Jun. 21, 2016.

(51) Int. Cl.
| | |
|---|---|
| *C12Q 1/68* | (2018.01) |
| *C12N 15/10* | (2006.01) |
| *C12N 15/11* | (2006.01) |
| *C40B 40/02* | (2006.01) |
| *C40B 50/06* | (2006.01) |
| *C12N 15/09* | (2006.01) |
| *C12N 9/22* | (2006.01) |

(52) U.S. Cl.
CPC ........... *C12N 15/1093* (2013.01); *C12N 9/22* (2013.01); *C12N 15/09* (2013.01); *C12N 15/102* (2013.01); *C12N 15/11* (2013.01); *C12N 15/111* (2013.01); *C40B 40/02* (2013.01); *C40B 50/06* (2013.01); *C12N 2310/20* (2017.05); *C12N 2320/10* (2013.01)

(58) Field of Classification Search
None
See application file for complete search history.

(56) References Cited

U.S. PATENT DOCUMENTS

| | | | |
|---|---|---|---|
| 2015/0067922 A1* | 3/2015 | Yang ................. | C12N 15/8245 800/298 |
| 2018/0002379 A1* | 1/2018 | Miller ................. | C07K 14/805 |
| 2018/0291372 A1* | 10/2018 | Lu ........................ | C12N 15/102 |

FOREIGN PATENT DOCUMENTS

| | | | | |
|---|---|---|---|---|
| WO | 2016/040594 A1 | 3/2016 | | |
| WO | WO-2016040594 A1 * | 3/2016 | ........... | C12N 15/102 |
| WO | 2016/183438 A1 | 11/2016 | | |

OTHER PUBLICATIONS

Zetsche et al in "Cpf1 Is a Single RNA-Guided Endonuclease of a Class 2 CRISPR-Cas System" (Cell 2015 vol. 163, pp. 759-771; IDS reference). (Year: 2015).*
Lennon et al ("A scalable, fully automated process for construction of sequence-ready barcoded libraries for 454" Genome Biology 2010, pp. 1-9; IDS reference). (Year: 2010).*
Hsu Dissertation (dated Aug. 22, 2014). (Year: 2014).*
Karvelis in "Rapid characterization of CRISPR-Cas9 protospacer adjacent motif sequence elements" (Genome Biology vol. 16:253; pp. 1-13; IDS reference). (Year: 2015).*
Karvelis et al. Rapid characterization of CRISPR-Cas9 protospacer adjacent motif sequence elements. Genome Biol Nov. 19, 2015 vol. 16 No. 253 pp. 1-13. Especially p. 3 fig 1, p. 10 col. 1 para 3.
Lennon et al. A scalable, fully automated process for construction of sequence-ready barcoded libraries for 454. Genome Biol Feb. 5, 2010 vol. 11 No. 2 pp. R15 1-9. Especially p. 5 fig 2.
Perli et al. Continuous genetic recording with self-targeting CRISPR-Cas in human cells. Science ePub Aug. 18, 2016 vol. 353 No. 6304 pp. aag0511 1-10. Especially p. 2 fig 1B and fig 1B legend, p. 2 col. 1 para 1 to p. 2 col. 2 para 1.

* cited by examiner

*Primary Examiner* — Catherine S Hibbert
(74) *Attorney, Agent, or Firm* — Banner & Witcoff, Ltd.

(57) ABSTRACT

A method of processing a collection of nucleic acid sequences is provided including connecting an adaptor to one or more or each nucleic acid sequence in the collection to create a processed nucleic acid template library, wherein the adaptor includes a first DNA sequence encoding a PAM sequence and at least a tracr mate.

32 Claims, 11 Drawing Sheets
Specification includes a Sequence Listing.

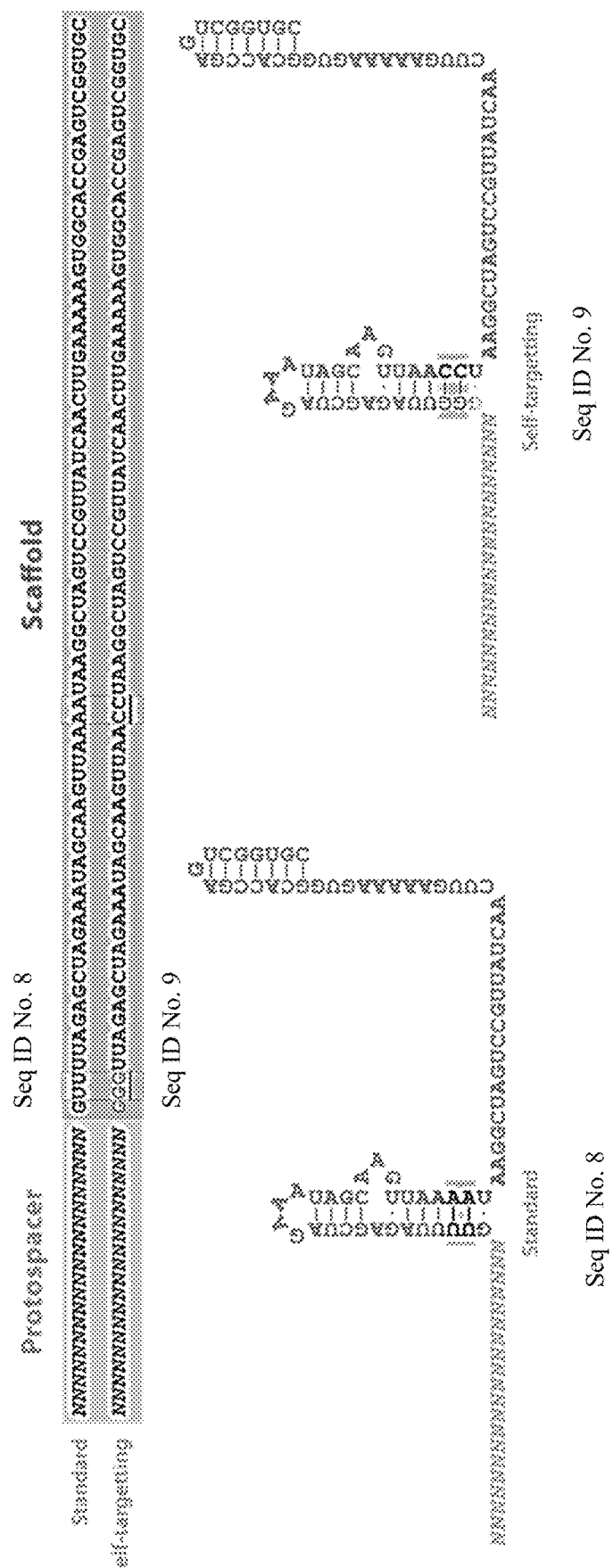

FIG. 7
stgRNA:Cas9 complexes are formed
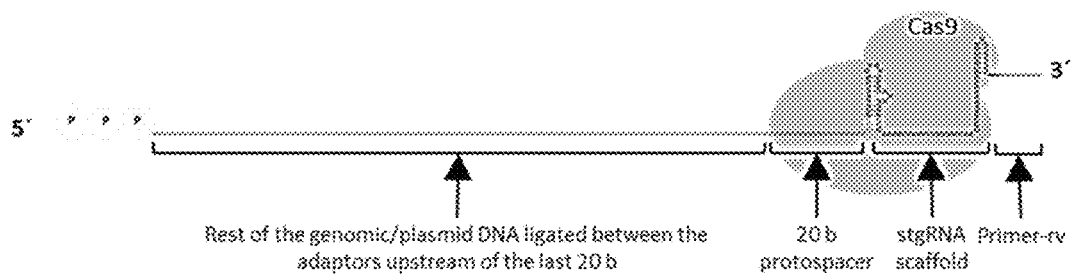
Footprinting
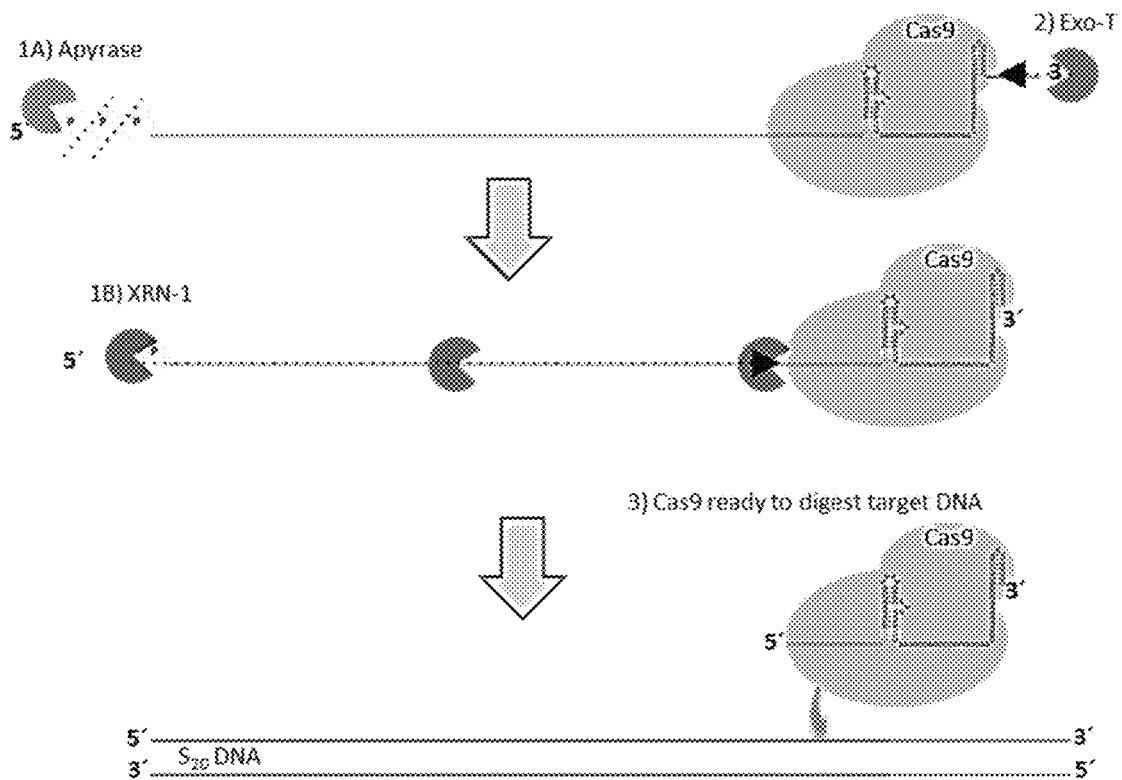

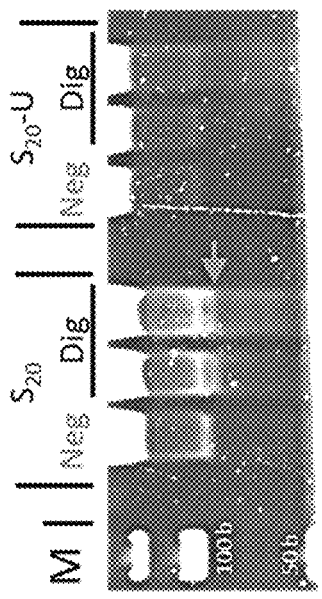
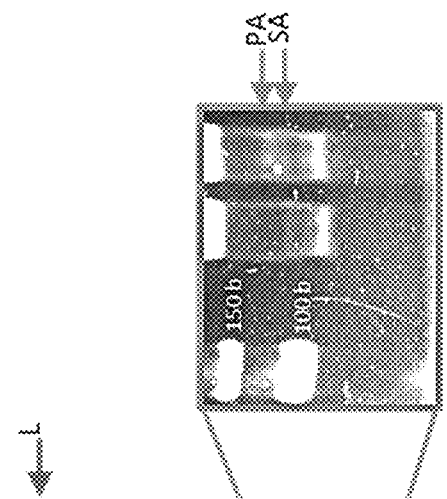
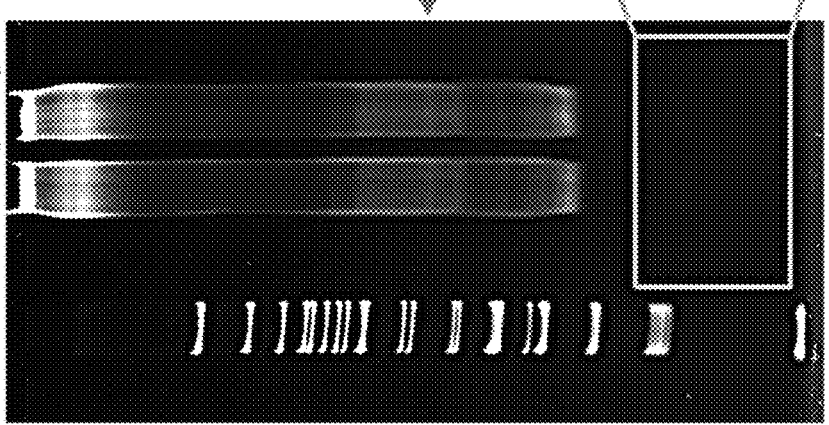
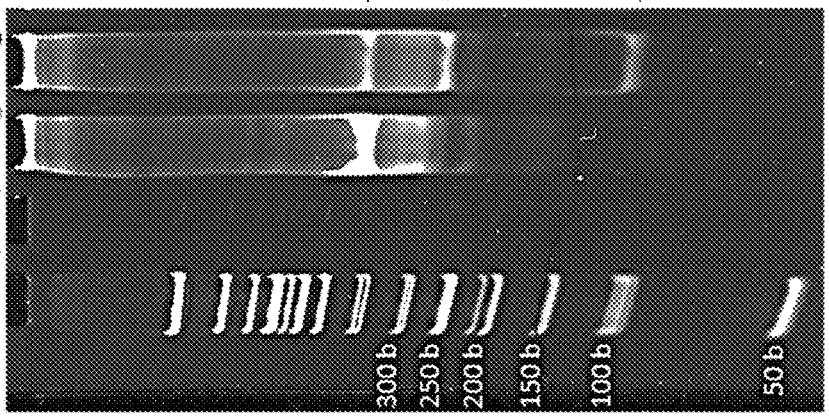
FIG. 8A  FIG. 8B  FIG. 8C

FREQUENCY-BASED MODULATION OF DIVERSE SPECIES IN A NUCLEIC ACID LIBRARY

RELATED APPLICATIONS

This application is a National Stage Application under 35 U.S.C. 371 of co-pending PCT application PCT/US17/38414 designating the United States and filed Jun. 21, 2017; which claims the benefit of U.S. provisional application No. 62/352,768 filed on Jun. 21, 2016 each of which are hereby incorporated by reference in their entireties.

STATEMENT OF GOVERNMENT INTERESTS

This invention was made with government support under MH103910 awarded by National Institutes of Health and DE-FG02-02ER63445 awarded by Department of Energy. The government has certain rights in the invention.

BACKGROUND

Amplification of a library of DNA molecules is an integral part of all contemporary molecular cloning, genetic engineering, and high-throughput sequencing applications. The most common methods of library amplification are polymerase chain reaction (Saiki R K, Scharf S, Faloona F, Mullis K B, Horn G T, Erlich H A, et al., Enzymatic amplification of beta-globin genomic sequences and restriction site analysis for diagnosis of sickle cell anemia, *Science,* 1985 Dec. 20; 230(4732):1350-4) and rolling circle amplification (Lizardi P M, Huang X. Zhu Z. Bray-Ward P, Thomas D C, Ward D C., Mutation detection and single-molecule counting using isothermal rolling-circle amplification. *Nat Genet.* 1998 July; 19(3):225-32). These amplification strategies may be used with a variety of goals in mind, including increasing the number of copies that are available from DNA molecules or adding desired sequences, known as adaptors, to amplicons.

Despite their very commonplace and versatile use, all forms of DNA library amplification have a fundamental limitation that reduces their effectiveness and scope of use. This limitation is known as "amplification bias" (See Acinas S G, Sarma-Rupavtarm R, Klepac-Ceraj V, Polz M F. PCR-Induced Sequence Artifacts and Bias: Insights from Comparison of Two 16S rRNA Clone Libraries Constructed from the Same Sample, *Appl Environ Microbiol.* 2005 Dec. 1:71(12):8966-9; Schloss P D, Gevers D, Westcott S L. Reducing the effects of PCR amplification and sequencing artifacts on 16S rRNA-based studies. Gilbert J A, editor, *PLoS One,* 2011 Dec. 14; 6(12):e27310; Aird D, Ross M G, Chen W-S, Danielsson M, Fennell T, Russ C, et al. Analyzing and minimizing PCR amplification bias in Illumina sequencing libraries, *Genome Biol.* 2011:12(2):R18; Daley T, Smith A D., Predicting the molecular complexity of sequencing libraries. *Nat Methods,* 2013 Apr. 24; 10(4):325-7; and Edgar R C, Flyvbjerg H., Error filtering, pair assembly and error correction for next-generation sequencing reads, *Bioinformatics* 2015 Nov. 1; 31(21):3476-82). Amplification bias is highly undesirable in most molecular biology and genetic techniques.

The underlying principle of amplification bias is that different amplicons—or DNA molecules—in a library have different sequences and are thus amplified with variable efficiencies: some sequences are amplified more while others are amplified less, and even to the point where members of the template library having low amplification may be masked by members of the template library having high amplification. As a result of this bias, representation of each molecule in the library becomes altered upon amplification. Since most sources of amplification bias are persistent and most amplification processes are cyclical, after enough cycles, amplification eventually and inevitably leads to an "amplified library" which may bear little resemblance to its parent or "template library." For example, any amplification of a DNA library biases the representation of various sequences in it as different sequences amplify with different efficiencies. As a result, through consecutive cycles of amplification, any DNA library becomes increasingly biased and will eventually lose most if not all of its diversity.

Accordingly, methods of modulating or reducing diverse species in a nucleic acid library are desirable.

SUMMARY

The present disclosure provides a method of modulating or reducing amplicons in a library, such as the most abundant amplicons in a library. In one aspect, members of the amplicon library may be removed from the library or otherwise rendered inoperative in the library. In particular, methods are directed to reversing the effects of amplification bias with respect to a DNA library amplification strategy generally and in PCR specifically.

According to one aspect, a DNA binding protein and a guide RNA are used to colocalize to one or more amplicons in an amplicon library and the colocalization complex modulates the target amplicon through binding of the co-localization complex, through enzymatic activity of the DNA binding protein or through an effector moiety bound to the DNA binding protein or the guide RNA or both. The disclosure contemplates use of a self-targeting guide RNA ("stgRNA") strategy or homing guide RNA (hgRNA). As is known in the art, a guide RNA includes a spacer sequence which is complementary to a target nucleic acid sequence, known as a protospacer sequence. A guide RNA also includes a tracr mate sequence connected to the spacer sequence. The tracr mate sequence may be referred to herein as a scaffold. The combination of a spacer sequence and a tracr mate sequence may be referred to in the art as a crRNA. A guide RNA also includes a tracrRNA sequence which hybridizes to the tracr mate sequence. The tracr mate sequence and the tracrRNA sequence may be connected, such as by a linker sequence and the combination may be referred to as a fusion or as a scaffold.

For purposes of the present disclosure, the protospacer sequence may be referred to as the double stranded sequence targeted by the guide RNA spacer sequence. While the guide RNA spacer sequence will bind to one strand of the protospacer sequence, i.e. the complement of the guide RNA spacer, the sequence of the guide RNA spacer may be described with respect to either strand of the protospacer sequence. For example, the guide RNA spacer sequence may be described as being complementary to one strand of the protospacer sequence while the guide RNA spacer sequence may be described as being identical to the other strand of the protospacer sequence. Accordingly, guide RNA spacer sequences may be described as being designed with respect to either strand. Should a guide RNA spacer sequence be described as being identical to a protospacer sequence, it is to be understood that the guide RNA spacer sequence is being designed with respect to the protospacer strand to which it will not bind. In this manner, the resulting guide RNA spacer sequence will bind to the other protospacer strand to which it is complementary.

According to one aspect, a DNA template including at least a protospacer adjacent motif sequence ("PAM sequence") is added to each amplicon in a library or collection as an adaptor. According to one aspect, a DNA template of a protospacer adjacent motif sequence ("PAM sequence") and at least a tracr mate sequence is added to each amplicon in a library or collection as an adaptor. This processing of the amplicon library or collection produces a processed library or collection. According to one aspect, a DNA template of PAM sequence and a scaffold including a tracr mate sequence and a tracrRNA sequence is added to each amplicon as an adaptor. According to one aspect, a DNA template of a PAM sequence and a scaffold including a tracr mate sequence, a linker and a tracrRNA sequence is added to each amplicon as an adaptor. Guide RNAs which can bind to the nucleic acid from which they are expressed, i.e. self-targeting guide RNAs, are generated, such as by transcription or other methods known to those of skill in the art, from the amplicons bearing the adaptors in vitro. As a result, a guide RNA is generated having a spacer sequence complementary to a portion of the amplicon from which it was transcribed ("the corresponding amplicon"), a PAM sequence and a scaffold sequence including at least a tracr mate sequence thereby generating a guide RNA that will target the corresponding amplicon in the library and, according to some embodiments, also form a colocalization complex with an RNA guided DNA binding protein. A tracr mate sequence and a tracrRNA, if not already present, can be added to the PAM sequence as needed by the DNA binding protein. A tracrRNA sequence, if not already present, can be added to the tracr mate sequence as needed by the DNA binding protein. The generated guide RNA can then be combined with an RNA guided DNA binding protein to target and form a co-localization complex with the associated amplicon within the library. The RNA guided DNA binding protein may be enzymatically active or nuclease null, but may have an effector group bound thereto. The guide RNA may have an effector group bound thereto. The formation of a colocalization complex results in modulation of the amplicon based on the binding and formation of the colocalization complex or based on the enzymatic function of the DNA binding protein itself, i.e. cutting or nicking, or any effector group, i.e. cutting or nicking enzyme, transcriptional modulator, detectable moiety, etc., that may be bound to either the DNA binding protein or guide RNA or both.

According to one aspect of the invention, self-targeting guide RNAs are expressed using transcription from the collection of DNA molecules with adaptor. The abundance of each transcription product correlates with the abundance of its corresponding DNA molecule in the processed library. This results in a library of self-targeting guide RNA or DNA binding protein/stgRNA complexes whose abundance is correlated to the abundance of each corresponding amplicon in the library. The amplicon library template, i.e., any amplicon library produced by an amplification step, is then combined with the stgRNA library and an RNA guided DNA binding protein, where a colocalization complex forms between the stgRNA, its corresponding amplicon and the DNA binding protein resulting in modulation of the amplicon. The library processed in this manner may be referred to as a processed library. According to one aspect of the present disclosure, the most abundant amplicons produce more of their own stgRNA, they will be modulated by the colocalization complex including the DNA binding protein and guide RNA more frequently, thereby reversing the PCR bias.

When the modulation described herein results in inactivation of the associate amplicon in the library, the amplicon is said to be removed or subtracted from the library. Such removal or subtraction may result from actual cutting or nicking of the amplicon, making it ineffective in the library or rendering it unable to be further amplified if one or more further amplification steps are carried out on the processed library. In this manner, the corresponding amplicon is physically eliminated from the amplicon library or collection. In this manner, a subpopulation of amplicons is physically eliminated from the amplicon library or collection. In this manner, the frequency of amplicons, i.e. relative abundance, in a library or collection, may be modulated or reduced or subtracted from the library or collection.

The methods described herein may be applied to a first library and a second library having members which partially overlap with the first library so as to select a subpopulation of the first library. The stgRNAs can be produced from the subpopulation of the second library and combined with a DNA binding protein. Treating or combining the first library with the stgRNAs generated from the second library and a DNA binding protein enzyme and driving the cutting or nicking or digestion or modulation reaction can modulate from the first library effectively all amplicons that are present in the subpopulation or the overlapping part of the second library.

The methods described herein may be applied to a first library and a second library having members which partially overlap with the first library so as to select a subpopulation of the first library. The stgRNAs can be produced from the subpopulation of the second library and combined with a DNA binding protein. Treating or combining the first library with the stgRNAs generated from the second library and a DNA binding protein enzyme and driving the cutting or nicking or digestion reaction to completion or near completion can cut and thus subtract from the first library effectively all amplicons that are present in the subpopulation or the overlapping part of the second library.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 2 shows sequence comparison between a standard guide RNA and a modified self-targeting guide RNA.

FIG. 7 is a schematic representation of the footprinting of the stgRNA:Cas9 complexes. Upper panel depicts formation of the stgRNA:Cas9 complexes. Lower panel depicts footprinting. On the 5' end of stgRNA the apyrase (orange circular sector) activity remove the phosphates γ and β paving the way for XRN-1 exonuclease activity (purple circular sector). On the 3' end Exo-T (green circular sector) exonuclease activity degrades the unprotected area.

FIGS. 8A-C are directed to electrophoretic analysis of Cas9 digestions. FIG. 8A depicts a gel directed to digestion of a $S_{20}$ plasmid library (pUC-19). FIG. 8B depicts a gel directed to digestion of a $S_{20}$ genomic library (*E. coli* MG1655). The size of the DNA fragments integrated between the adaptors varies between libraries. The area of the gel where the digestion bands appear has been magnified and contrasted. FIG. 8C depicts a gel directed to digestion of genomic $S_{20}$ and $S_{20}$—U libraries amplified from the same template. The area shown is restricted to the region of the gel where the cutting bands appear. Legend: Blue arrow, L, starting Library: orange arrows, digestion products PA (Promoter adaptor plus DNA providing the protospacer) and SA (Scaffold adaptor): M, molecular size marker; Neg, negative control for the digestion, no stgRNA present: Dig, digestion reaction. When PA and SA are not indicated by the orange arrows the size of both cut products is indistinguishable.

FIG. 9B is a plot similar to FIG. 9A showing the coverage of *E. coli* genome in the non-adjusted (Neg1) sample and another non-adjusted (Neg2) sample, showing no significant alteration in the bias of the coverage.

DETAILED DESCRIPTION

Embodiments of the present disclosure are directed to the generation of self-targeting guide RNAs or homing guide RNAs from a library of nucleic acids, such as DNA amplicons, processed to include an adaptor having at least a PAM sequence and optionally, at least a tracr mate sequence. Embodiments of the present disclosure are directed to the generation of self-targeting guide RNAs or homing guide RNAs from a library of nucleic acids, such as DNA amplicons, processed to include an adaptor having a PAM sequence and at least a tracr mate sequence. Self-targeting or homing guide-RNAs useful in the present disclosure are discussed in Kalhor R, Mali P. Church G M. Rapidly evolving homing CRISPR barcodes, bioRxiv [Internet] 2016 May 27; available from: http://www.biorxiv.org/content/early/2016/05/20/053058 hereby incorporated by reference in its entirety, and Perli S, Cui C, Lu T K., Continuous Genetic Recording with Self-Targeting CRISPR-Cas in Human Cells, bioRxiv [Internet], 2016 May 20; available from: http://biorxiv.org/content/early/2016/05/20/053058, hereby incorporated by reference in its entirety.

Figure 1A:
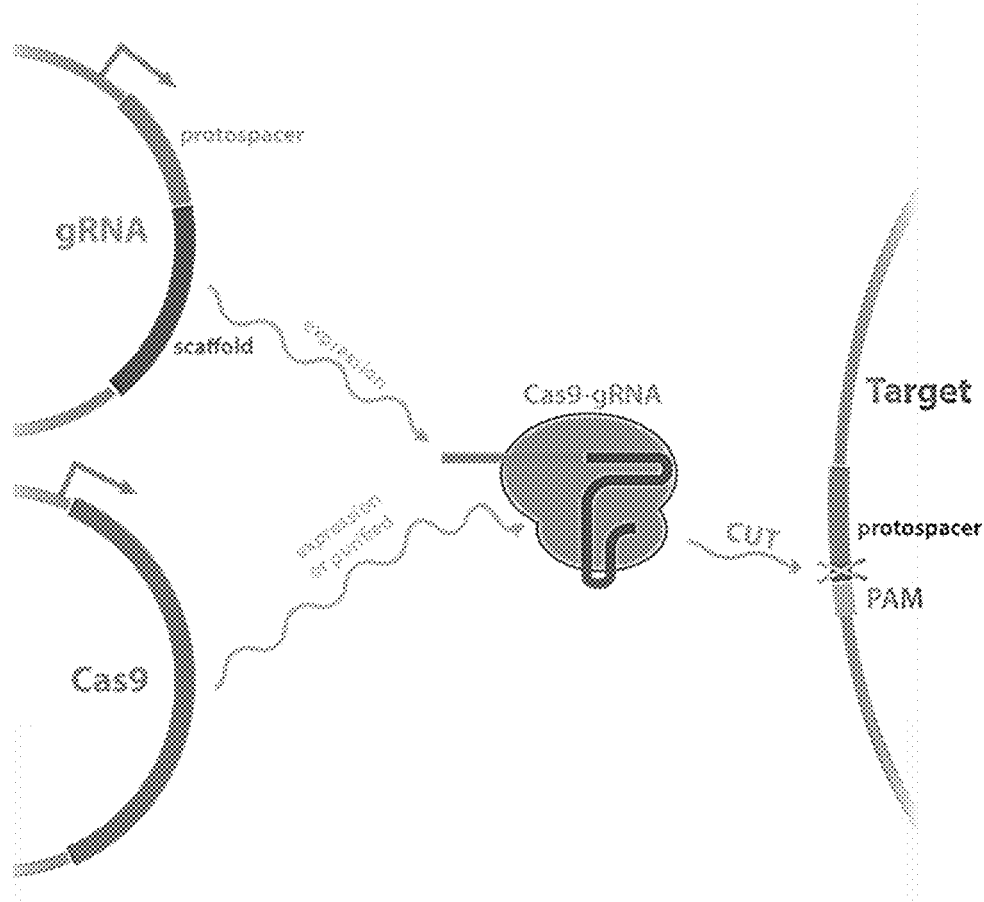
FIG. 1A is a schematic showing a standard application of the CRISPR/Cas9 system.

FIG. 1A is a schematic showing a standard application of the CRISPR/Cas9 system. See in general, Konermann, Silvana, et al. "Genome-scale transcriptional activation by an engineered CRISPR-Cas9 complex." Nature (2014), hereby incorporated by reference in its entirety. The Cas9 protein is introduced into a cell, such as by being expressed in situ such as by introduction of a vector or by introduction of a purified Cas protein. A guide RNA is introduced into a cell, such as being expressed through transcription or added as a purified RNA, where the Cas9 protein and the gRNA form a complex and cut endogenous target loci that match both the protospacer and the PAM. The vector encoding the guide RNA, however, is not a target of the Cas9/gRNA complex because while it contains a cognate protospacer sequence it does not contain a PAM sequence adjacent to the protospacer.

Figure 1B:
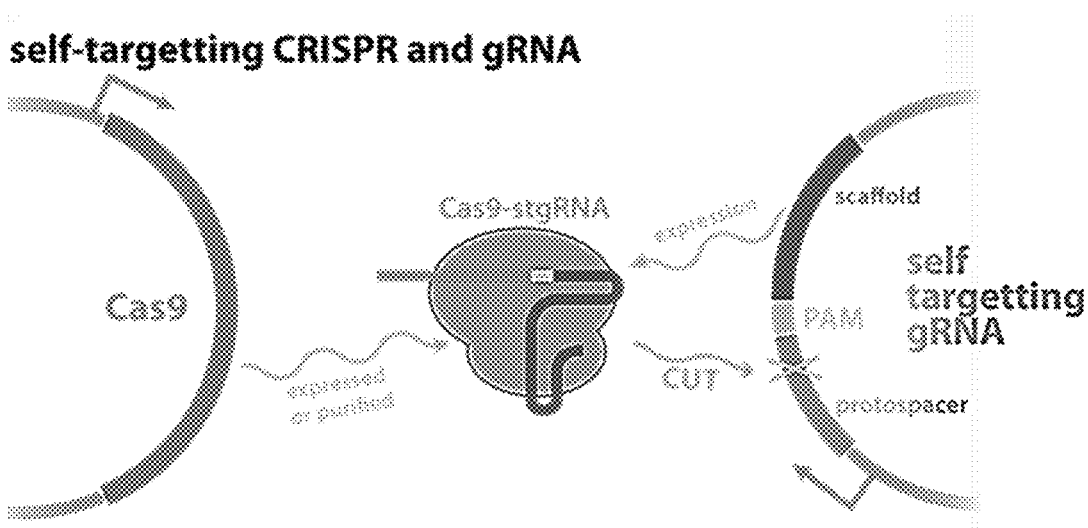
FIG. 1B is a schematic showing an exemplary application of the self-targeting CRISPR/Cas9 system.

FIG. 1B is a schematic showing an exemplary application of the self-targeting CRISPR/Cas9 system. A PAM motif is engineered in the nucleic acid sequence encoding the guide RNA sequence which does not affect the guide RNA function. The Cas9 protein and modified guide RNAs containing both a cognate protospacer sequence and a PAM sequence adjacent to the protospacer are introduced by DNA vectors into a cell and are expressed where the Cas9 protein and the modified gRNA form a complex and cut the vector encoding the guide RNA, as it includes both a PAM sequence and a protospacer sequence.

FIG. 2 depicts an example of engineering a self-targeting guide RNA to be used with *S. pyogenes* Cas9 as the RNA guided DNA binding protein so that the guide RNA may identify the nucleic acid sequence from which it was generated and without disrupting the guide RNA function. A nucleic acid sequence encoding a standard guide RNA sequence including a protospacer sequence and a scaffold sequence is shown. A nucleic acid sequence encoding a self-targeting guide RNA sequence including a protospacer sequence and a scaffold sequence is also shown. Two nucleotides that are located on the 5' end of the scaffold—between the scaffold and the protospacer—are mutated to match the PAM sequence for *Streptococcus pyogenes* Cas9 (NGG). Compensatory mutations have been introduced further downstream in the scaffold to restore secondary structure and gRNA function. The expected secondary structures of normal and self-targeting gRNAs and how the compensatory mutations in the stgRNA scaffold restore its secondary structure are shown.

According to one aspect, a method is provided of processing a collection of nucleic acid sequences, such as DNA sequences, including connecting an adaptor to one or more or each nucleic acid sequence in the collection to create a processed nucleic acid template library, wherein the adaptor includes a first DNA sequence encoding at least a PAM sequence and at least a tracr mate sequence, which may be referred to as a scaffold. According to one aspect, the method further includes connecting a promoter to each nucleic acid sequence in the collection. According to one aspect, a promoter is connected to each nucleic acid sequence in the collection and the processed nucleic acid template library is amplified to create an amplicon library. Methods of connecting the adaptor or promoter include ligation, transposition or PCR or other methods known to those of skill in the art.

Converting the nucleic acid sequence with the adaptor sequence to RNA generates a guide RNA where the sequence of each amplicon that resides upstream of the scaffold provides a protospacer, and the generated guide RNA will include the corresponding spacer sequence, thereby forming an operative guide RNA that uniquely identifies its parent amplicon. In this manner, the guide RNA that is generated from the DNA amplicon having the adaptor as described herein is referred to as a self-targeting guide RNA, to the extent that it targets the sequence from which it was generated. Combining such guide RNA molecules with an RNA-guided DNA binding protein, such as a Cas protein of a CRISPR system as is known in the art, and the library of amplicons used to generate the guide RNA molecules results in co-localization of the guide RNA and the RNA-guided DNA binding protein with its corresponding amplicon. If the RNA-guided DNA binding protein is a nuclease or a nickase, the RNA-guided DNA binding protein will cut or nick the target amplicon thereby removing it from the library. The frequency of each amplicon can dictate the severity of its cutting and depletion from the library. These principles can be combined with various selection and amplification strategies to obtain desired adjustments or subtraction of molecules from a DNA library.

According to one aspect, the first DNA sequence further encodes a tracrRNA sequence. The first DNA sequence further encodes a tracrRNA sequence connected to the tracr mate sequence. The first DNA sequence further encodes a tracrRNA sequence connected to the crRNA by a linker sequence. According to one aspect, the first DNA sequence further encodes a tracrRNA sequence connected to the crRNA sequence by a linker sequence forming a guide RNA scaffold sequence. According to one aspect, the first DNA sequence further encodes a tracrRNA sequence connected to the crRNA sequence by a linker sequence forming a guide RNA scaffold sequence, wherein the guide RNA scaffold sequence is a CRISPR guide RNA scaffold sequence.

According to one aspect, the first DNA sequence further encodes a tracrRNA sequence connected to the tracr mate sequence by a linker sequence forming a guide RNA scaffold sequence, wherein the guide RNA scaffold sequence is a modified guide RNA scaffold sequence including the PAM sequence such that it is capable of self-targeting or homing activity. According to one aspect, the PAM sequence is immediately adjacent to the tracr mate sequence. According to one aspect, the PAM sequence is located relative to the tracr mate sequence such that expression of the first DNA sequence results in a self-targeting or homing guide RNA when combined with a tracrRNA. According to one aspect, the PAM sequence is located upstream or downstream of the tracr mate sequence. According to one aspect, the PAM sequence is located inside the tracr mate sequence.

According to one aspect, the collection of nucleic acid sequences includes DNA sequences. According to one aspect, the collection of nucleic acid sequences has unknown nucleic acid sequences, i.e. the nucleic acid sequences are unknown. The methods described herein allow one of skill to modulate members of a collection of nucleic acids, such as to remove amplification bias, without knowing the actual sequences of the nucleic acids in the collection. According to one aspect, the collection of nucleic acid sequences includes double stranded DNA sequences. According to one aspect, the collection of nucleic acid sequences includes DNA sequences selected from the group consisting of chromosomal DNA, mitochondrial DNA, viral DNA or metagenomics DNA sequences. According to one aspect, the collection of nucleic acid sequences includes synthetic DNA sequences. According to one aspect, the collection of nucleic acid sequences includes RNA sequences. According to one aspect, the collection of nucleic acid sequences includes DNA sequences generated by reverse transcription of RNA sequences. According to one aspect, each member of the processed nucleic acid template library includes a barcode unique to that member.

The present disclosure provides creating a guide RNA library from corresponding members of a processed nucleic acid template library as described herein wherein each member of the guide RNA library includes a spacer sequence complementary to a protospacer sequence of the corresponding member of the processed nucleic acid template library. According to one aspect, the processed nucleic acid template library may be amplified to produce an amplicon library before generating a guide RNA library so that the guide RNA library is generated from the amplicon library. According to one aspect, each member of the guide RNA library correlates in number with its corresponding member of the library from which is was generated, such as an amplicon library. According to one aspect, the guide RNA library is prepared by transcribing members of the processed nucleic acid template library using an RNA polymerase to create corresponding members of the guide RNA library wherein each member of the guide RNA library includes a spacer sequence complementary to a protospacer sequence of the member of the processed DNA template library from which it was transcribed. According to one aspect, the RNA polymerase is T7 RNA polymerase or SP6 RNA polymerase or *E. coli* RNA polymerase. Other suitable RNA polymerases are known to those of skill in the art.

The present disclosure provides a method of creating a guide RNA library from corresponding members of a processed nucleic acid template library as describe herein wherein each member of the guide RNA library includes a spacer sequence complementary to a protospacer sequence of the corresponding member of the processed nucleic acid template library, and combining the processed nucleic acid template library including one or more target nucleic acids, the guide RNA library and one or more RNA-guided DNA binding proteins to form one or more colocalization complexes between a target nucleic acid, a guide RNA and an RNA-guided DNA binding protein in a manner to modulate the one or more target nucleic acids. The processed nucleic acid template library may be amplified before the guide RNA library is generated. In this case the guide RNA library is generated from the amplicon library.

The RNA-guided DNA binding protein is more fully described herein and includes an RNA-guided DNA binding protein nuclease, a thermophilic RNA-guided DNA binding protein nuclease, an RNA-guided DNA binding protein nickase, a nuclease null RNA-guided DNA binding protein. According to one aspect, the RNA-guided DNA binding protein includes a Cas nuclease, a Cas nickase or a nuclease null Cas protein. A Cas as described herein may be any Cas known to those of skill in the art that may be directed to a target nucleic acid using an RNA as known to those of skill in the art. The Cas may be wild type or a homolog or ortholog thereof, such as Cpf1 (See, Zetsche, Bernd et al., Cpf1 Is a Single RNA-Guided Endonuclease of a Class 2

CRISPR-Cas System, *Cell*, Volume 163, Issue 3, pgs 759-771, hereby incorporated by reference in its entirety). The Cas may be nonnaturally occurring, such as an engineered Cas as disclosed in Slaymaker, I. M., Gao, L., Zetsche. B., Scott, D. A., Yan, W. X, and Zhang, F., 2016. Rationally engineered Cas9 nucleases with improved specificity. *Science*, 351(6268), pp. 84-88 hereby incorporated by reference in its entirety. The Cas may have one or more nucleolytic domains altered to prevent nucleolytic activity, such as with a Cas nickase or nuclease null or "dead" Cas. Aspects of the present disclosure utilize nicking to effect cutting of one strand of the target nucleic acid. A nuclease null or "dead" Cas may have a nuclease attached thereto to effect cutting, cleaving or nicking of the target nucleic acid. Such nucleases are known to those of skill in the art.

According to one aspect, the RNA-guided DNA binding protein includes a Cas9 nuclease, a Cas9 nickase or a nuclease null Cas9 protein. According to one aspect, the RNA-guided DNA binding protein includes a spCas9 nuclease, a spCas9 nickase or a nuclease null spCas9 protein. According to one aspect, the RNA-guided DNA binding proteins includes *S. pyogenes* Cas9, *S. thermophilis* Cas9, *N. meningitides* Cas9. *T. denticola* Cas9, or *S. aureus* Cas9. According to one aspect, the RNA-guided DNA binding protein includes a Cpf1 nuclease, a Cpf1 nickase or a nuclease null Cpf1 protein.

According to one aspect, the RNA-guided DNA binding protein includes an effector moiety or group attached thereto. The RNA-guided DNA binding protein may be a nuclease null RNA-guided DNA binding protein including an effector moiety or group attached thereto. An effector moiety or group includes a modulator moiety or group. Exemplary effector groups or moieties include a detectable moiety, a transcriptional regulator, a protein domain, a nuclease, a phosphatase, deaminase, kinase, polynucleotide kinase, Uracil-DNA glycosylase, nuclease, endonuclease, exonuclease, site-specific nuclease, ligase, polymerase, recombinase, methyl-transferase, fluorescent protein, beta-galactosidase, antibody, scFv single-chain variable fragment of an antibody, nanobody, transcriptional activator, transcriptional repressor, biotin, streptavidin, aptamer, nanoparticle, gold nanoparticle, quantum dot, magnetic bead, paramagnetic particle, or oligonucleotide.

According to one aspect, the guide RNA includes an effector moiety or group attached thereto. An effector moiety or group includes a modulator moiety or group. Exemplary effector groups or moieties include a detectable moiety, a transcriptional regulator, a protein domain, a nuclease, a phosphatase, deaminase, kinase, polynucleotide kinase, Uracil-DNA glycosylase, nuclease, endonuclease, exonuclease, site-specific nuclease, ligase, polymerase, recombinase, methyl-transferase, fluorescent protein, beta-galactosidase, antibody, scFv single-chain variable fragment of an antibody, nanobody, transcriptional activator, transcriptional repressor, biotin, streptavidin, aptamer, nanoparticle, gold nanoparticle, quantum dot, magnetic bead, paramagnetic particle, or oligonucleotide.

According to the methods described herein, the target nucleic acids in the processed library or amplicon library thereof are modulated. Modulating may refer to altering the target nucleic acid so that it is removed from the library or otherwise rendered ineffective in the library. Modulating may also refer to the function of the effector group or moiety attached to the RNA-guided DNA binding protein or guide RNA. A target nucleic acid may be modulated by being cut or nicked by the RNA-guided DNA binding protein. A target nucleic acid may be modulated by being bound by the RNA-guided DNA binding protein. A target nucleic acid may be modulated by the function of the effector group or moiety attached to the RNA-guided DNA binding protein or the guide RNA. A target nucleic acid may be modulated by being bound by the RNA-guided DNA binding protein and the function of the effector group or moiety attached to the RNA-guided DNA binding protein or the guide RNA.

According to one aspect, one or more target amplicons are disproportionately amplified and are cut to reduce amplification bias in the amplicon library. According to one aspect, one or more target amplicons are cut to remove the one or more target amplicons from the amplicon library. According to one aspect, one or more target amplicons are cut to enrich non-target amplicons in the amplicon library.

According to one aspect, the processed library is a library of DNA molecules, a library of nucleic acid molecules or a library of double stranded DNA molecules and the one or more target nucleic acids are cut to remove the one or more target nucleic acids from the library. According to one aspect, the processed library is a library of DNA molecules, a library of nucleic acid molecules or a library of double stranded DNA molecules and the one or more target nucleic acids are cut to enrich non-target nucleic acids in the processed nucleic acid library.

The disclosure provides a method of modulating members of a collection of nucleic acids including the steps of connecting a first DNA sequence encoding a PAM sequence, a tracr mate sequence and a tracrRNA sequence to each nucleic acid sequence in the collection to create a processed nucleic acid template library, wherein a portion of the nucleic acid sequence, the PAM sequence, the tracr mate sequence and the tracrRNA sequence form a self-targeting or homing guide RNA template sequence, amplifying the processed nucleic acid template library to create an amplicon library, creating a guide RNA library from corresponding members of the processed nucleic acid template library wherein each member of the guide RNA library includes a spacer sequence complementary to a protospacer sequence of the corresponding member of the processed nucleic acid template library, and combining the amplicon library including one or more target nucleic acids, the guide RNA library and one or more RNA-guided DNA binding proteins to form one or more colocalization complexes between a target nucleic acid, a guide RNA and an RNA-guided DNA binding protein in a manner to modulate the one or more target nucleic acids to produce a modulated collection of nucleic acids. According to one aspect, the modulated collection of nucleic acids is amplified and combined with the guide RNA library and one or more RNA-guided DNA binding proteins to further modulate the collection of nucleic acids. According to one aspect, the modulated collection of nucleic acids is repeatedly amplified and combined with the guide RNA library and one or more RNA-guided DNA binding proteins to further modulate the collection of nucleic acids.

The disclosure provides a method of modulating members of a first collection of nucleic acids using members of a second collection of nucleic acids including the steps of connecting a first DNA sequence encoding a PAM sequence, a tracr mate and a tracrRNA sequence to each nucleic acid sequence in both collections to create first and second processed nucleic acid template libraries, wherein a portion of the nucleic acid sequence, the PAM sequence, the tracr mate sequence and the tracrRNA sequence form a self-targeting or homing guide RNA template sequence, amplifying the second processed nucleic acid template library to create an amplicon library from the second collection of nucleic acids, creating a guide RNA library from corresponding members of the processed nucleic acid template library of the second collection of nucleic acids wherein each member of the guide RNA library includes a spacer sequence complementary to a protospacer sequence of the corresponding member of the processed nucleic acid template library, and combining the first amplicon library including one or more target nucleic acids, the guide RNA library and one or more RNA-guided DNA binding proteins to form one or more colocalization complexes between a target nucleic acid, a guide RNA and an RNA-guided DNA binding protein in a manner to modulate the one or more target nucleic acids in the first nucleic acid library.

The disclosure provides a method of reducing amplification bias in a library of DNA amplicons including the steps of connecting a promoter sequence and a first DNA sequence encoding a PAM sequence, a tracr mate sequence and a tracrRNA sequence to each member of a DNA library to create a processed DNA template library, wherein a portion of the member of the DNA library, the PAM sequence, the tracr mate sequence and the tracrRNA sequence form a self-targeting or homing guide RNA template sequence, transcribing members of the processed DNA template library using an RNA polymerase to create corresponding members of a guide RNA library wherein each member of the guide RNA library includes a spacer sequence complementary to a protospacer sequence of the member of the processed DNA template library from which it was transcribed, amplifying members of the processed DNA template library to produce a library of DNA amplicons of the processed DNA template library, combining the DNA amplicons with a Cas nuclease and the corresponding members of the guide RNA library, wherein, for each of a plurality of amplicons, a colocalization complex is formed by the Cas nuclease, a target amplicon and a corresponding guide RNA, and wherein the Cas nuclease cuts the target amplicon to reduce amplification bias in the library of DNA amplicons to create an adjusted amplified library.

The present disclosure provides a method of reducing amplification bias in a library of DNA amplicons including the steps of connecting a promoter sequence and a first DNA sequence encoding a PAM sequence, a tracr mate sequence and a tracrRNA sequence to each member of a DNA library to create a processed DNA template library, wherein a portion of the member of the DNA library, the PAM sequence, the tracr mate sequence and the tracrRNA sequence form a self-targeting or homing guide RNA template sequence, and amplifying members of the processed DNA template library in a polymerase chain reaction (PCR), wherein a thermophilic Cas nuclease and a thermophilic RNA polymerase are added to the PCR reaction, and where in each amplification cycle, the RNA polymerase transcribes a guide RNA from members of the DNA template library and Cas nuclease forms a colocalization complex with transcribed guide RNAs and target amplicons corresponding to guide RNAs, and wherein the Cas nuclease cuts the target amplicon to reduce amplification bias in the library of DNA amplicons to create an adjusted amplified library.

The present disclosure provides a method of enriching for target DNA having low amplification efficiency within an original DNA library including the steps of connecting a promoter sequence and a first DNA sequence encoding a PAM sequence, a tracr mate sequence and a tracrRNA sequence to each to each member of a DNA library to create a processed DNA template library, wherein a portion of the member of the DNA library, the PAM sequence, the tracr sequence and the tracrRNA sequence form a self-targeting or homing guide RNA template sequence, amplifying members of the processed DNA template library to produce a library of DNA amplicons of the processed DNA template library, transcribing members of the library of DNA amplicons using an RNA polymerase to create corresponding members of a guide RNA library wherein each member of the guide RNA library includes a spacer sequence complementary to a protospacer sequence of the member of the library of DNA amplicons from which it was transcribed, combining the library of DNA amplicons with a Cas nuclease and the corresponding members of the guide RNA library, wherein, for each of a plurality of amplicons, a colocalization complex is formed by the Cas nuclease, a target amplicon and a corresponding guide RNA, and wherein the Cas nuclease cuts the target amplicon to create an adjusted amplified library, and amplifying the adjusted amplified library to create a library enriched in the target DNA having low amplification efficiency compared to the original DNA library. According to one aspect, the library enriched in the target DNA is selected as the original library and the steps of connecting, amplifying, transcribing and combining are repeated.

Exemplary RNA-Guided DNA Binding Proteins

RNA guided DNA binding proteins are readily known to those of skill in the art to bind to DNA for various purposes. Such DNA binding proteins may be naturally occurring. DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews. Microbiology*, Vol. 9, June 2011, pp. 467-477 including all supplementary information hereby incorporated by reference in its entirety.

In general, bacterial and archaeal CRISPR-Cas systems rely on short guide RNAs in complex with Cas proteins to direct degradation of complementary sequences present within invading foreign nucleic acid. See Deltcheva. E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli*. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type 11 CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. *Journal of Bacteriology* 190, 1390 (February, 2008). Additional useful Cas proteins are from *S. thermophilis* or *S. aureus*.

Three classes of CRISPR systems are generally known and are referred to as Type I. Type II or Type III). According to one aspect, a particular useful enzyme according to the present disclosure to cleave dsDNA is the single effector enzyme, Cas9, common to Type II. See K. S. Makarova et al., Evolution and classification of the CRISPR-Cas systems. *Nature reviews. Microbiology* 9, 467 (June, 2011) hereby incorporated by reference in its entirety. Within bacteria, the Type II effector system consists of a long pre-crRNA transcribed from the spacer-containing CRISPR locus, the multifunctional Cas9 protein, and a tracrRNA important for gRNA processing. The tracrRNAs hybridize to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9. TracrRNA-crRNA fusions are contemplated for use in the present methods.

According to one aspect, the enzyme of the present disclosure, such as Cas9 unwinds the DNA duplex and searches for sequences matching the crRNA to cleave. Target recognition occurs upon detection of complementarity between a "protospacer" sequence in the target DNA and the remaining spacer sequence in the crRNA. Importantly, Cas9 cuts the DNA only if a correct protospacer-adjacent motif (PAM) is also present at the 3' end. According to certain aspects, different protospacer-adjacent motif can be utilized. For example, the *S. pyogenes* system requires an NGG sequence, where N can be any nucleotide. *S. thermophilus* Type II systems require NGGNG (see P. Horvath, R Barrangou. CRISPR/Cas, the immune system of bacteria and archaea. *Science* 327, 167 (Jan. 8, 2010) hereby incorporated by reference in its entirety and NNAGAAW (see H. Deveau et al., Phage response to CRISPR-encoded resistance in *Streptococcus thermophilus. Journal of bacteriology* 190, 1390 (February, 2008) hereby incorporated by reference in its entirety), respectively, while different *S. mutans* systems tolerate NGG or NAAR (see J. R, van der Ploeg, Analysis of CRISPR in *Streptococcus mutans* suggests frequent occurrence of acquired immunity against infection by M102-like bacteriophages. *Microbiology* 155, 1966 (June, 2009) hereby incorporated by reference in its entirety. Bioinformatic analyses have generated extensive databases of CRISPR loci in a variety of bacteria that may serve to identify additional useful PAMs and expand the set of CRISPR-targetable sequences (see M. Rho, Y. W. Wu, H. Tang, T. G. Doak, Y. Ye, Diverse CRISPRs evolving in human microbiomes. *PLoS genetics* 8, e1002441 (2012) and D. T. Pride et al., Analysis of streptococcal CRISPRs from human saliva reveals substantial sequence diversity within and between subjects over time. *Genome research* 21, 126 (January, 2011) each of which are hereby incorporated by reference in their entireties.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinek et al., *Science* 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: *Methanococcus maripaludis* C7; *Corynebacterium diphtheriae; Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1: *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1: *Bifidobacterium longum* DJO10A; *Slackia heliotrinireducens* DSM 20476; *Persephonella marina* EX H1: *Bacteroides fragilis* NCTC 9434: *Capnocytophaga ochracea* DSM 7271. *Flavobacterium psychrophilum* JIP02 86; *Akkermansia muciniphila* ATCC BAA 835; *Roseiflexus castenholzii* DSM 13941; *Roseiflexus* RS1: *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua; Lactobacillus casei; Lactobacillus rhanmnosus* GG; *Lactobacillus salivarius* UCC118; *Streptococcus agalactiae* A909: *Streptococcus agalactiae* NEM316: *Streptococcus agalactiae* 2603; *Streptococcus dysgalactiae equisimilis* GGS 124; *Streptococcus equi zooepidemicus* MGCS10565: *Streptococcus gallolyticus* UCN34 uid46061: *Streptococcus gordonii* Challis subst CH1; *Streptococcus mutans* NN2025 uid46353; *Streptococcus mutans; Streptococcus pyogenes* M1 GAS; *Streptococcus pyogenes* MGAS5005; *Streptococcus pyogenes* MGAS2096: *Streptococcus pyogenes* MGAS9429: *Streptococcus pyogenes* MGAS10270; *Streptococcus pyogenes* MGAS6180; *Streptococcus pyogenes* MGAS315: *Streptococcus pyogenes* SSI-1; *Streptococcus pyogenes* MGAS10750: *Streptococcus pyogenes* NZ131; *Streptococcus thermophiles* CNRZ1066: *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10: *Finegoldia magna* ATCC 29328; *Eubacterium rectale* ATCC 33656; *Mycoplasma gallisepticum; Mycoplasma* mobile 163K1 *Mycoplasma penetrans: Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1: *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442: *Neisseria meningitides* alpha14: *Neisseria meningitides* Z2491: *Desulfovibrio salexigens* DSM 2638; *Campylobacter jejuni* doylei 269 97; *Campylobacter jejuni* 81116: *Campylobacter jejuni: Campylobacter lari* RM2100; *Helicobacter hepaticus: Wolinella succinogenes; Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida; Francisella tularensis novicida* U112: *Francisella tularensis holarctica; Francisella tularensis* FSC 198; *Francisella tularensis tularensis; Francisella tularensis* WY96-3418; and *Treponema denticola* ATCC 35405. The Cas9 protein may be referred by one of skill in the art in the literature as Csn1. An exemplary *S. pyogenes* Cas9 protein sequence is provided in Deltcheva et al., *Nature* 471, 602-607 (2011) hereby incorporated by reference in its entirety.

Modification to the Cas9 protein is a representative embodiment of the present disclosure. CRISPR systems useful in the present disclosure are described in R. Barrangou, P. Horvath, CRISPR: new horizons in phage resistance and strain identification. *Annual review of food science and technology* 3, 143 (2012) and B. Wiedenheft, S. H. Sternberg, J. A. Doudna. RNA-guided genetic silencing systems in bacteria and archaea. *Nature* 482, 331 (Feb. 16, 2012) each of which are hereby incorporated by reference in their entireties.

According to certain aspects, the DNA binding protein is altered or otherwise modified to inactivate the nuclease activity. Such alteration or modification includes altering one or more amino acids to inactivate the nuclease activity or the nuclease domain. Such modification includes removing the polypeptide sequence or polypeptide sequences exhibiting nuclease activity. i.e. the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes polypeptide sequences modified to inactivate nuclease activity or removal of a polypeptide sequence or sequences to inactivate nuclease activity. The nuclease-null DNA binding protein retains the ability to bind to DNA even though the nuclease activity has been inactivated. Accordingly, the DNA binding protein includes the polypeptide sequence or sequences required for DNA binding but may lack the one or more or all of the nuclease sequences exhibiting nuclease activity. Accordingly, the DNA binding protein includes the polypeptide sequence or sequences required for DNA binding but may have one or more or all of the nuclease sequences exhibiting nuclease activity inactivated.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase. An exemplary DNA binding protein is an RNA guided DNA binding protein nuclease of a Type II CRISPR System, such as a Cas9 protein or modified Cas9 or homolog of Cas9. An exemplary DNA binding protein is a Cas9 protein nickase. An exemplary DNA binding protein is an RNA guided DNA binding protein of a Type II CRISPR System which lacks nuclease activity. An exemplary DNA binding protein is a nuclease-null or nuclease deficient Cas9 protein.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. See Jinek et al., *Science* 337, 816-821 (2012). According to an additional aspect, the amino acids include D839 and N863. According to one aspect, one or more or all of D10, H840, D839 and H863 are substituted with an amino acid which reduces, substantially eliminates or eliminates nuclease activity. According to one aspect, one or more or all of D10, H840, D839 and H863 are substituted with alanine. According to one aspect, a Cas9 protein having one or more or all of D10, H840, D839 and H863 substituted with an amino acid which reduces, substantially eliminates or eliminates nuclease activity, such as alanine, is referred to as a nuclease-null Cas9 ("Cas9Nuc") and exhibits reduced or eliminated nuclease activity, or nuclease activity is absent or substantially absent within levels of detection. According to this aspect, nuclease activity for a Cas9Nuc may be undetectable using known assays, i.e. below the level of detection of known assays.

According to one aspect, the Cas9 protein, Cas9 protein nickase or nuclease null Cas9 includes homologs and orthologs thereof which retain the ability of the protein to bind to the DNA and be guided by the RNA. According to one aspect, the Cas9 protein includes the sequence as set forth for naturally occurring Cas9 from *S. thermophiles* or *S. pyogenes* or *S. aureus* and protein sequences having at least 30%, 40%, 50%, 60%, 70%, 80%, 90%, 95%, 98% or 99% homology thereto and being a DNA binding protein, such as an RNA guided DNA binding protein.

An exemplary CRISPR system includes the *S. thermophiles* Cas9 nuclease (ST1 Cas9) (see Esvelt K M. et al., Orthogonal Cas9 proteins for RNA-guided gene regulation and editing, Nature Methods, (2013) hereby incorporated by reference in its entirety). An exemplary CRISPR system includes the *S. pyogenes* Cas9 nuclease (Sp. Cas9), an extremely high-affinity (see Sternberg, S. H., Redding, S., Jinek, M., Greene, E. C. & Doudna, J. A. DNA interrogation by the CRISPR RNA-guided endonuclease Cas9. *Nature* 507, 62-67 (2014) hereby incorporated by reference in its entirety), programmable DNA-binding protein isolated from a type II CRISPR-associated system (see Garneau, J. E. et al. The CRISPR/Cas bacterial immune system cleaves bacteriophage and plasmid DNA. *Nature* 468, 67-71 (2010) and Jinek, M. et al. A programmable dual-RNA-guided DNA endonuclease in adaptive bacterial immunity. *Science* 337, 816-821 (2012) each of which are hereby incorporated by reference in its entirety). According to certain aspects, a nuclease null or nuclease deficient Cas 9 can be used in the methods described herein. Such nuclease null or nuclease deficient Cas9 proteins are described in Gilbert, L. A. et al. CRISPR-mediated modular RNA-guided regulation of transcription in eukaryotes. *Cell* 154, 442-451 (2013): Mali, P. et al. CAS9 transcriptional activators for target specificity screening and paired nickases for cooperative genome engineering. *Nature biotechnology* 31, 833-838 (2013); Maeder, M. L. et al. CRISPR RNA-guided activation of endogenous human genes. *Nature methods* 10, 977-979 (2013); and Perez-Pinera, P. et al. RNA-guided gene activation by CRISPR-Cas9-based transcription factors. *Nature methods* 10, 973-976 (2013) each of which are hereby incorporated by reference in its entirety. The DNA locus targeted by Cas9 (and by its nuclease-deficient mutant, "dCas9" precedes a three nucleotide (nt) 5'-NGG-3' "PAM" sequence, and matches a 15-22-nt guide or spacer sequence within a Cas9-bound RNA cofactor, referred to herein and in the art as a guide RNA. Altering this guide RNA is sufficient to target Cas9 or a nuclease deficient Cas9 to a target nucleic acid. In a multitude of CRISPR-based biotechnology applications (see Mali, P., Esvelt, K. M. & Church, G. M. Cas9 as a versatile tool for engineering biology. *Nature methods* 10, 957-963 (2013); Hsu, P. D., Lander, E. S. & Zhang, F. Development and Applications of CRISPR-Cas9 for Genome Engineering. *Cell* 157, 1262-1278 (2014): Chen, B. et al. Dynamic imaging of genomic loci in living human cells by an optimized CRISPR/Cas system. *Cell* 155, 1479-1491 (2013): Shalem, O. et al. Genome-scale CRISPR-Cas9 knockout screening in human cells. *Science* 343, 84-87 (2014); Wang, T., Wei, J. J., Sabatini, D. M. & Lander, E. S. Genetic screens in human cells using the CRISPR-Cas9 system. *Science* 343, 80-84 (2014); Nissim, L., Perli, S. D., Fridkin, A., Perez-Pinera, P. & Lu, T. K. Multiplexed and Programmable Regulation of Gene Networks with an Integrated RNA and CRISPR/Cas Toolkit in Human Cells. *Molecular cell* 54, 698-710 (2014); Ryan, O. W. et al. Selection of chromosomal DNA libraries using a multiplex CRISPR system. *eLife* 3 (2014); Gilbert, L. A. et al. Genome-Scale CRISPR-Mediated Control of Gene Repression and Activation. *Cell* (2014); and Citorik, R. J., Mimee, M. & Lu, T. K. Sequence-specific antimicrobials using efficiently delivered RNA-guided nucleases. *Nature biotechnology* (2014) each of which are hereby incorporated by reference in its entirety), the guide is often presented in a so-called sgRNA (single guide RNA), wherein the two natural Cas9 RNA cofactors (gRNA and tracrRNA) are fused via an engineered loop or linker.

According to one aspect, the Cas9 protein is an enzymatically active Cas9 protein, a Cas9 protein wild-type protein, a Cas9 protein nickase or a nuclease null or nuclease deficient Cas9 protein. Additional exemplary RNA-guided DNA binding proteins includes Cas9 proteins include Cas9 proteins attached to, bound to or fused with functional proteins such as transcriptional regulators, such as transcriptional activators or repressors, a Fok-domain, such as Fok 1, an aptamer, a binding protein, PP7, MS2 and the like. The nuclease null Cas9 protein and the guide RNA colocalize to the target nucleic acid or the nucleic acid encoding the guide RNA resulting in binding but not cleaving of the target nucleic acid. The activity or transcription of the target nucleic acid is regulated by such binding. The Cas9 protein can further comprise a transcriptional regulator or DNA modifying protein attached thereto. Exemplary transcriptional regulators are known to a skilled in the art and include VPR. VP64, P65 and RTA. Exemplary DNA-modifying enzymes are known to a skilled in the art and include Cytidine deaminases, APOBECs, Fok1, endonucleases and DNases.

Exemplary Guide RNA

Embodiments of the present disclosure are directed to the use of a RNA-guided DNA binding protein/guide RNA system, such as a CRISPR/Cas system and, in particular, a guide RNA which may include one or more of a spacer sequence, a tracr mate sequence and a tracr sequence. The term spacer sequence is understood by those of skill in the art and may include any polynucleotide having sufficient complementarity with a target nucleic acid sequence to hybridize with the target nucleic acid sequence and direct sequence-specific binding of a CRISPR complex to the target sequence. According to certain aspects, an exemplary spacer sequence is between 10 and 30 nucleotides in length. According to certain aspects, an exemplary spacer sequence is between 15 and 25 nucleotides in length. An exemplary spacer sequence is between 18 and 22 nucleotides in length. An exemplary spacer sequence is 20 nucleotides in length.

The guide RNA may be formed from a spacer sequence covalently connected to a tracr mate sequence (which may be referred to as a crRNA) and a separate tracr sequence, wherein the tracr mate sequence is hybridized to a portion of the tracr sequence. According to certain aspects, the tracr mate sequence and the tracr sequence are connected or linked such as by covalent bonds by a linker sequence, which construct may be referred to as a fusion of the tracr mate sequence and the tracr sequence. The linker sequence referred to herein is a sequence of nucleotides, referred to herein as a nucleic acid sequence, which connect the tracr mate sequence and the tracr sequence. Accordingly, a guide RNA may be a two component species (i.e., separate crRNA and tracr RNA which hybridize together) or a unimolecular species (i.e., a crRNA-tracr RNA fusion, often termed an sgRNA).

Tracr mate sequences and tracr sequences are known to those of skill in the art, such as those described in US 2014/0356958 and as shown in FIG. 2. An exemplary tracr mate sequence and tracr sequence is N20 to N8-gttttagagcta-gaaatagcaagttaaaataaaaggctagtccgttatcaacttgaaaaagtggcac-cgagtcggtgctttttt with N20-8 being the number of nucleotides complementary to a target locus of interest.

According to certain aspects, the tracr mate sequence is between about 17 and about 27 nucleotides in length. According to certain aspects, the tracr sequence is between about 65 and about 75 nucleotides in length. According to certain aspects, the linker nucleic acid sequence is between about 4 and about 6.

According to certain methods, two or more or a plurality of guide RNAs may be used in the practice of certain embodiments.

According to certain aspects, the guide RNA is between about 10 to about 500 nucleotides. According to one aspect, the guide RNA is between about 20 to about 100 nucleotides. According to certain aspects, the spacer sequence is between about 10 and about 500 nucleotides in length and particularly between about 14 and about 22 nucleotides in length. According to certain aspects, the tracr mate sequence is between about 10 and about 500 nucleotides in length. According to certain aspects, the tracr sequence is between about 10 and about 100 nucleotides in length. According to certain aspects, the linker nucleic acid sequence is between about 4 and about 100 nucleotides in length, and particularly between about 4 and about 6 nucleotides in length.

Exemplary Transcriptional Regulators

According to one aspect, the RNA-guided DNA binding proteins or the guide RNA may include one or more transcriptional regulator proteins or domains attached, bound, tethered, connected or fused thereto, as effector moieties or groups. According to one aspect, the transcriptional regulator protein or domain is a transcriptional activator. According to one aspect, the transcriptional regulator protein or domain upregulates expression of the target nucleic acid. According to one aspect, the transcriptional regulator protein or domain is a transcriptional repressor. According to one aspect, the transcriptional regulator protein or domain downregulates expression of the target nucleic acid. Transcriptional activators and transcriptional repressors can be readily identified by one of skill in the art based on the present disclosure. Transcriptional regulator proteins or domains which are transcriptional activators include VP16 and VP64 and others readily identifiable by those skilled in the art based on the present disclosure. See Zhang et al., *Nature Biotechnology* 29, 149-153 (2011) hereby incorporated by reference in its entirety. The transcriptional regulatory domains correspond to targeted loci. Accordingly, aspects of the present disclosure include methods and materials for localizing transcriptional regulatory domains to targeted loci of target nucleic acids by fusing, connecting or joining such domains to an RNA-guided DNA binding protein such as Cas or a guide RNA.

Target Nucleic Acid

Target nucleic acids within a library as described herein include any nucleic acid sequence to which a co-localization complex as described herein can be useful to either cut, nick or regulate or modulate. Target nucleic acids include nucleic acid sequences, such as genomic nucleic acids, such as genes, capable of being expressed into proteins. For purposes of the present disclosure, a co-localization complex can bind to or otherwise co-localize with the target nucleic acid at or adjacent or near the target nucleic acid and in a manner in which the co-localization complex may have a desired effect on the target nucleic acid. One of skill based on the present disclosure will readily be able to identify or design guide RNAs and Cas9 proteins which co-localize to a target nucleic acid. One of skill will further be able to identify transcriptional regulator proteins or domains which likewise co-localize to a target nucleic acid.

Detectable Domains or Proteins or Labels

According to one aspect, the RNA-guided DNA binding protein or guide RNA may include one or more detectable proteins or domains or labels or markers attached, bound, connected or fused thereto, which can then be detected or imaged to identify the location of the target nucleic acid sequence. Detectable labels or markers can be readily identified by one of skill in the art based on the present disclosure. Aspects of the methods described herein may make use of epitope tags and reporter gene sequences. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, betaglucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

The following examples are set forth as being representative of the present disclosure. These examples are not to be construed as limiting the scope of the present disclosure as these and other equivalent embodiments will be apparent in view of the present disclosure, figures and accompanying claims.

Example I

Modulation of Diverse Species in a DNA Library

Figure 3A:
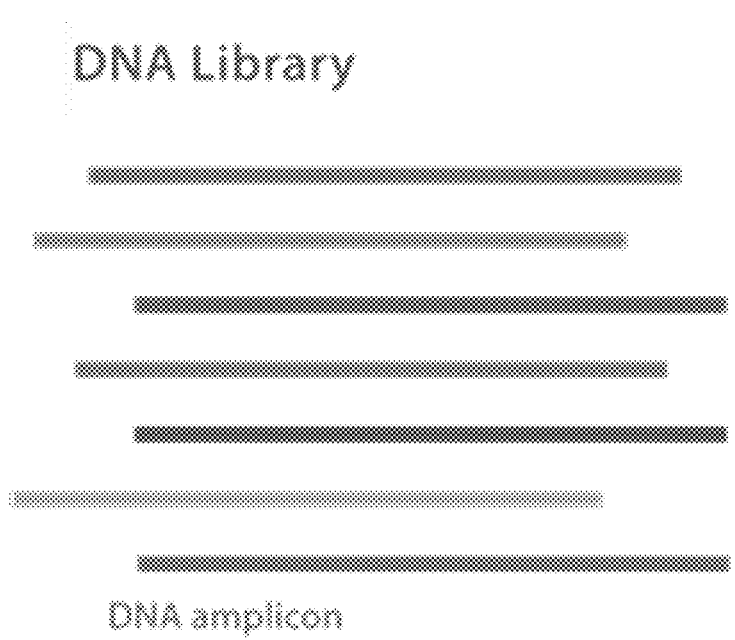
FIG. 3 is a schematic showing steps in a method of generating self-targeting guide RNAs which are used to adjust amplicon frequencies in a DNA amplicon collection or library.
Figure 3B:
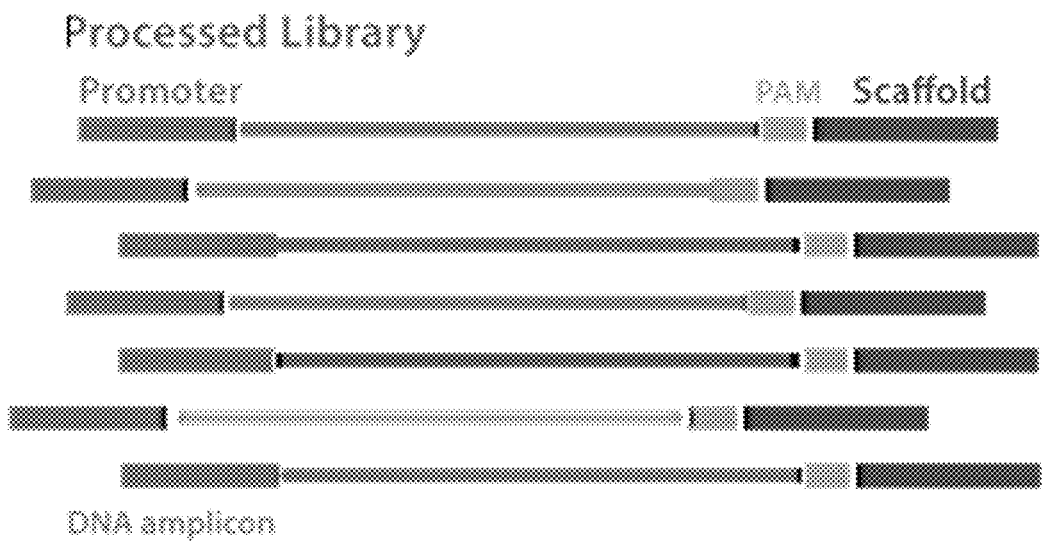

The present disclosure provides methods of modulating or adjusting or removing members of a collection of nucleic acids such as DNA sequences. FIG. 3A-3F depict method steps A through F in a method of removing, or subtracting or adjusting diversity in a library of DNA amplicons. According to the method of this example, PCR has been used to create a library of amplicons from a template library of DNA fragments as shown in FIG. 3A. S. pyogenes Cas9 is the RNA Guided DNA binding protein. As shown in FIG. 3B, the DNA library is processed such that every amplicon is attached on one end to a promoter and on the other end to the S. pyogenes scaffold, i.e. a tracr mate sequence or the combination of a tracer mate sequence and a tracrRNA sequence. The promoter can be any promoter recognized by an available RNA polymerase so as to enable production of RNA from each DNA molecule. Examples of applicable RNA polymerases include but are not limited to T7 and SP6 RNA polymerases.

The stgRNA scaffold should be added such that the NGG PAM sequence (FIG. 2) is placed exactly adjacent to a desired amplicon sequence which is the protospacer sequence. Addition of these promoter and stgRNA adaptor elements to all amplicons in a library can be achieved using various methods, including ligation, transposition, and PCR as described in the literature.

Figure 3C:
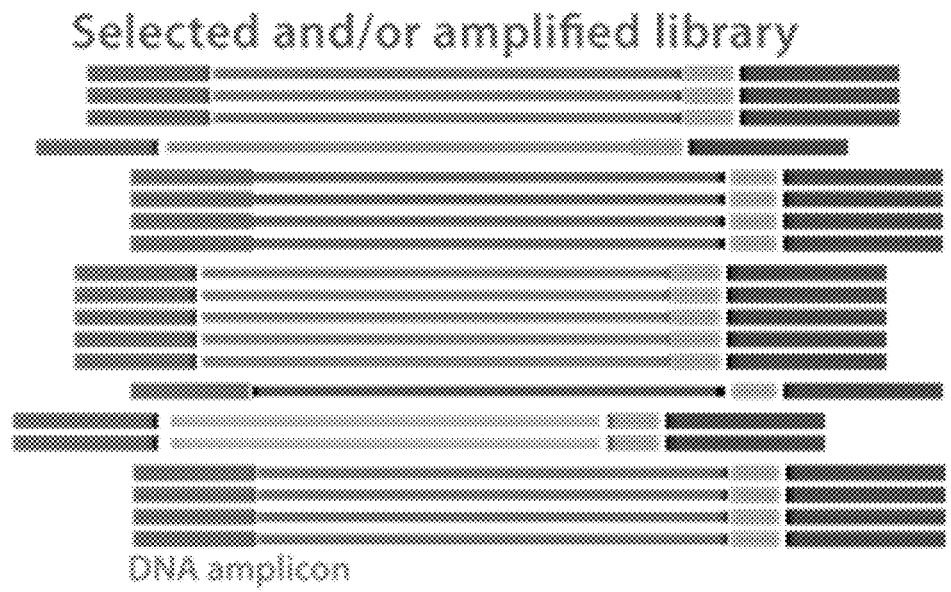
Figure 3D:
Figure 3E:
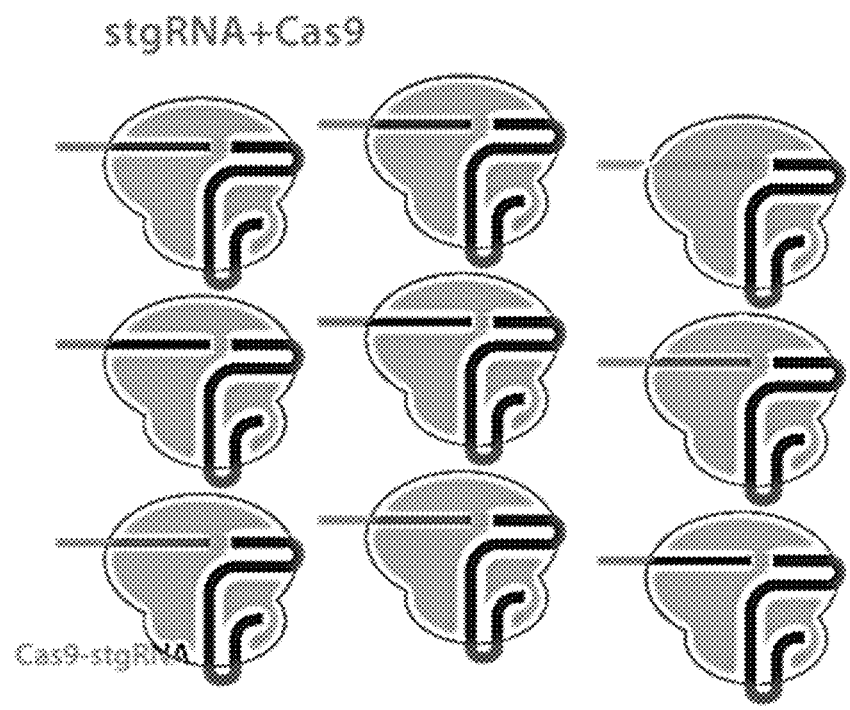
Figure 3F:
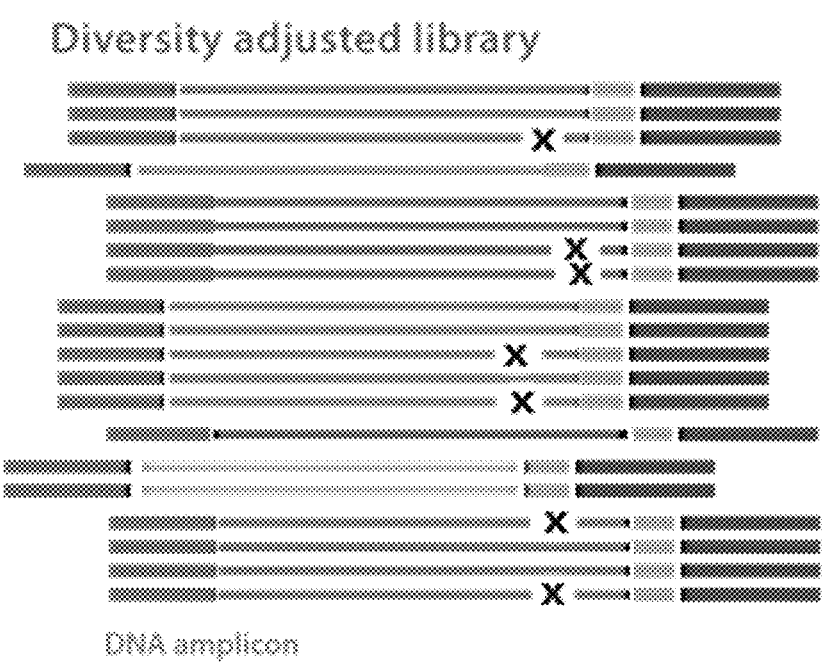

After addition of the adaptors, the library can be subjected to selection or amplification methods as depicted in FIG. 3C. For instance, primers that bind upstream of the promoter and downstream of the scaffold can be used in a PCR reaction to amplify all or a subset of the library. The amplified subset may be selected or random. Selecting a subset can be accomplished by using primers that identify specific barcodes that mark various subsets right downstream of the promoter or upstream of the scaffold. Alternatively, the library can be used without selection or amplification. Once a derivative of a library with appropriate adaptors is prepared (processed library), an aliquot of the processed library can be subjected to transcription using the relevant RNA polymerase as depicted in FIG. 3D. This transcription results in production of self-targeting guide RNAs from the library of amplicons. The frequency of each stgRNA sequence correlates with the frequency of its parent amplicon in the selected subset of the original library. Self-targeting guide RNAs from the transcription mixture is then combined with purified SpCas9 protein to form stgRNA-Cas9 complexes as shown in FIG. 3E. These complexes are active and will digest, according to stgRNA abundance, digestion time, and other parameters, their cognate DNA molecules. The complexes can thus be used to deplete the selected amplicons from the original library, or they can applied to an independent library with the stgRNA adaptors to subtract the parts of this independent library that overlap with the part of the library subset that was used to transcribe the stgRNAs as shown in FIG. 3F. Once an amplicon is digested, it cannot amplify in subsequent rounds of PCR and is thus eliminate from the target library.

Example II

Removing Bias from a PCR Library

Figure 4:
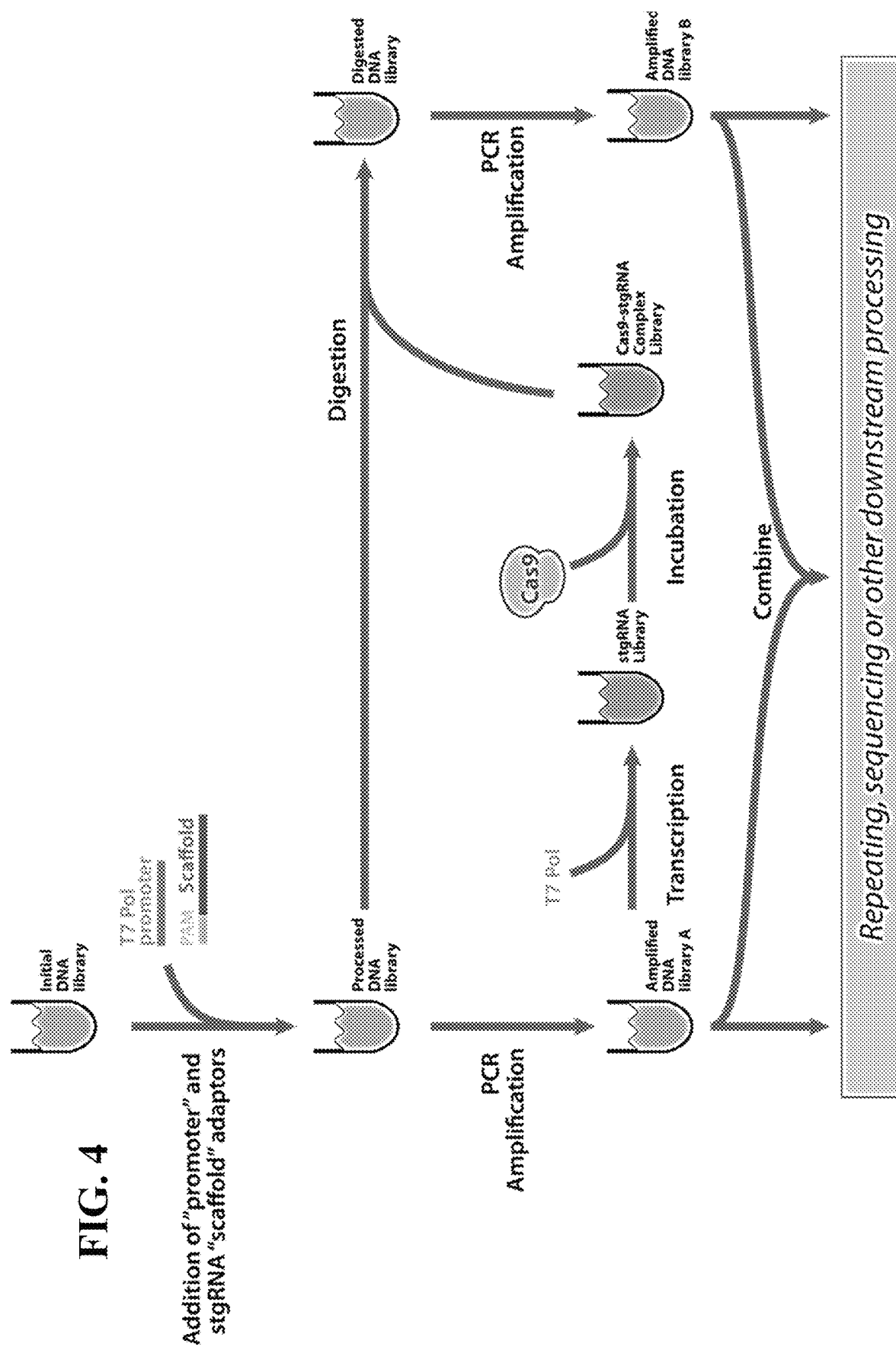
FIG. 4 is a schematic showing steps in a method to balance the diversity in a DNA library.

The present disclosure provides methods of removing bias from a PCR library, such as by amplifying fragments that are less efficiently amplified by PCR and may become depleted because of PCR bias. As shown in FIG. 4, an initial DNA library, which can itself be a result of DNA extraction from a sample or product of a PCR reaction, is processed to ligate the T7 RNA polymerase promoter on one end and the S. pyogenes scaffold on the other end. The resulting processed DNA library is then amplified in a PCR reaction using primers that bind upstream of the promoter sequence and downstream of the scaffold to obtain amplified DNA library A. Amplified DNA library A will be biased such that the more efficient amplicons have increased abundances while the less efficient amplicons have reduced abundances. An aliquot of amplified DNA library A is then subjected to in vitro transcription using T7 RNA polymerase. The resulting stgRNA library, which embodies the PCR biases of library A, is mixed with purified SpCas9 protein to create a Cas9-stgRNA complex library A. In the Cas9-stgRNA complex library A, the stgRNAs of the more efficient amplicons from the initial DNA library have a higher frequency. Therefore, far more complexes exist that target the abundant amplicons in amplified DNA library A than those that target the less abundant amplicons. The Cas9-stgRNA complex library A can then be used to treat an aliquot of the initial DNA library resulting in depletion of the abundant molecules of library A in this digested library, i.e. treating an aliquot of the initial processed DNA library with Cas9-stgRNA complex library A results in a digested DNA library where amplicons that are more efficient in PCR, and thus more abundant in amplified DNA library A, will be depleted drastically. This digested DNA library can then be used as template for another PCR reaction to produce an Amplified DNA Library B in which the less efficient amplicons of the initial DNA library are now enriched. Either the amplified DNA library B, or a mixture of it with amplified DNA library A, represents a new DNA library with a more balanced distribution of amplicon frequencies that reverses PCR bias effects. Combining amplified libraries A and B at appropriate ratios (which can involve 0% of library A) produces a library with a better representation of both the more efficient and the less efficient amplicons in the original library than amplified library A does by itself. Furthermore, this process can be repeated iteratively to gradually enrich for the least efficient amplicons in the original library. For instance, an amplified library C can be produced by using stgRNA-Cas9 complexes from both library A and library B to digest the original library. Library C will now represents molecules that don't efficiently amplify in either library A or library B and can be used on its own or in an appropriate mixture with libraries A and B to obtain optimal results. The iterative process can be extended a plurality of rounds N, producing amplified libraries D through N, each of which representing a different subset of the amplicons in the original library.

Example III

Specific Applications

The methods described herein can be use in the curation of metagenomic samples and of RNAseq libraries. In the case of the metagenomic libraries, the objective is often to find a new gene or cluster of genes that encode for a desired enzymatic function or pathway. However, far too often the signal of the species of interest in the metagenomics samples is masked by the most dominant species in the community of microorganism which tend to be well studied. A stgRNA-based library adjustment can be used on specific metagenomics samples to effectively increase the probability of detecting the minority species. These minority species don't amplify well using standard PCR due to a combination of PCR bias and their low starting frequencies. In the case of RNAseq libraries, it is well documented that the preparation of RNA libraries requires many steps designed to avoid the overwhelmingly dominant fractions of 16S and 18S ribosomal RNAs, which are the most abundant RNAs in prokaryotic and eukaryotic cells, respectively. Methods described herein can be used to eliminate or deplete rRNA sequences in an RNA seq library.

Example IV

Application to an *E. coli* Genomic DNA Library and Reduction of PCR Bias

The methods described herein were used to prepare a library of *E. coli* genomic DNA which was amplified and diversity adjusted according to the method described in FIG. 3. A negative control without diversity adjustment was used. The digestion of the adjusted library was assessed in vitro and its distribution and coverage of the *E. coli* genome was analyzed by high throughput sequence. The library was effectively digested in vitro reducing PCR bias and improving coverage after sequencing.

Adaptor Design and Preparation:

Two specific adaptors were designed in order to prepare the DNA library for treatment. These adaptors will flank every DNA fragment in the library. First, the promoter adaptor carries a T7 RNA polymerase promoter ($P_{T7}$). Its sequence was based in recommendations by Promega (Madison, Wis.) and iGEM Parts Registry (world wide website parts.igem.org/Promoters/CatalogT7). A sequencing primer Primer-fw is fused to the 5' of $P_{T7}$ that is used for rapid PCR amplification and indexing for sequencing on Illumina platforms. The scaffold adaptor contains the stgRNA scaffold sequence. As described herein, the transcript of this sequence is used for Cas9 recognition and cutting of the target/template DNA sequences. A sequencing primer Primer-rv is fused to the 3' of the stgRNA scaffold that is similar to primer-fw and is used for PCR amplification and sequencing on Illumina platforms.

Once ligated to the amplicons in the library, the relative positions of the adaptors is as follows (only coding strand showed):

```
5' Primer-fw_P_T7-[LIBRARY_FRAGMENT]-stgRNA_
scaffold_Primer-rv 3'
5'ACACTCTTTCCCTACACGACGCTCTTCCGATCTAATTAATACGAC

TCACTATAGGGAGA

[LIBRARY_FRAGMENT]
GGGTTAGAGCTAGAAATAGCAAGTTAACCTAAGGCTACTCCGTTATCAAC

TTGAAAAAGTGGCACCGAGTCGGTGCTAGATCGGAAGAGCACACGTCTGA

ACTCCAGTC 3'
```

The adaptor sequences were obtained in their dsDNA form by ordering both strands separately as oligonucleotides. With the aim to reduce the ligation of the two adaptors between them excluding bridging dsDNA molecules from samples, a truncated version of one of the oligonucleotides necessary to reconstitute each adaptor was used:

```
Promoter adaptor:
5' . . . ACGACGCTCTTCCGATCTAATTAATACGAC

TCACTATAGGGAGA 3'

3' GAGAAGGCTAGATTAATTATGCTGAGTGATATCCCTCT 5'

Scaffold adaptor:
5'GGGTTAGAGCTAGAAATAGCAAGTTAACCTAAGGCTAG 3'

3'CCCAATCTCGATCTTTATCGTTCAATTGGATTCCGATCAGGCAA

T . . . 5'
```

The oligonucleotides that reconstitute dsDNA were hybridized by being incubated together in the presence of 200 uM salt, incubation at 95° C. for 1 minute followed by reducing temperature from 95° C. to 20° C. at a rate of 1° C./min to allow for annealing.

Library preparation was performed as follows.

Extraction: The treatment presented here is applicable to any library of DNA sequences regardless of their origin. Other methods of library preparation that can produce a similar outcome are known to those familiar with the art. The protocol presented herein was developed working with DNA collections originating from both plasmid and genomic sources. Plasmid DNA from *Escherichia coli* NEB 5α F' I$^q$ (pUC-19) and genomic DNA from *E. coli* MG1655 were extracted using commercially available kits (QIAprep Spin Miniprep Kit and DNeasy Blood & Tissue Kit, Qiagen, Germany).

Figure 5:
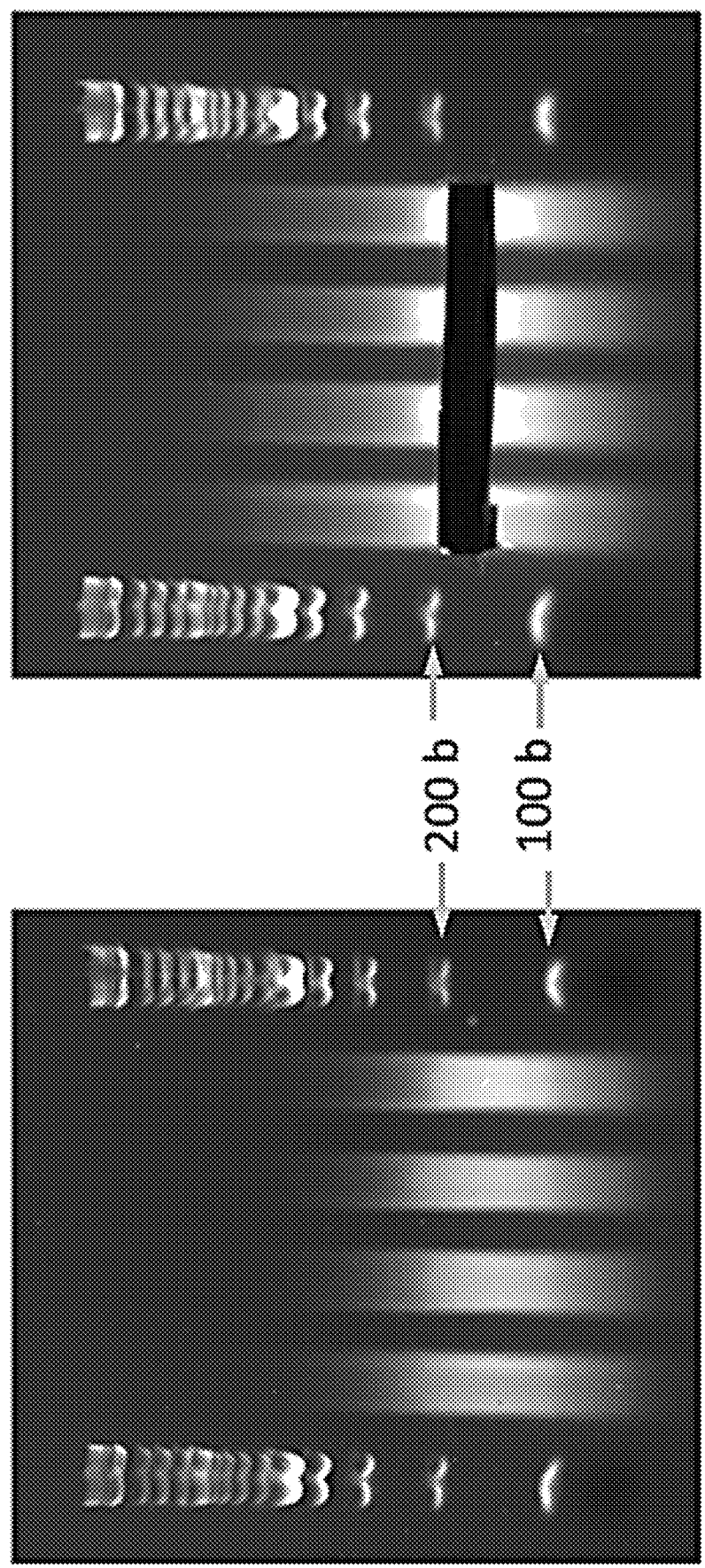
FIG. 5 depicts gels of a fragmented library after Covaris S2 treatment. Left panel: 2% agarose gel showing 4 lanes of DNA library sample after Covaris S2 treatment flanked by 2 molecular size marker lanes (NEB 2-log; NEB. Ipswich. Mass.). Right panel: Left panel gel showing the region extracted for DNA purification. The particular DNA library shown in this figure as an example corresponds to *E. coli* MG1655 genome.

Shearing: Plasmid and genome preparations were sheared in a Covaris $S_2$ ultrasonicator (Covaris, Woburn, Mass.) following the manufacturer's instructions. The desired target size was 200 bp. Bands of approximately to 200 bp were extracted from an agarose gel and purified as shown in FIG. 5.

End-repair: The purified samples were end-repaired, to create blunt and phosphorylated DNA ends, to make them suitable for a clean ligation process to the adaptors reconstituted as dsDNA. The end-repair reaction was carried out according to standard end-repair protocols on the DNA purified after shearing (above) with a cocktail of enzymes comprised of Klenow, T4 DNA polymerase and T4 polynucleotide kinase (Enzymatics, Beverly, Calif.).

Adaptor ligation: Reconstituted adapters were ligated to the end-repaired DNA using T4 ligase in a standard rapid ligation reaction (Enzymatics, Beverly, Calif.) to produce adaptor ligated products.

Strand displacement: Without purification, the adaptor ligated products were subjected to a strand-displacement process so that the truncated oligonucleotides of the adapters can be displaced to create the full adaptor sequence on each side. The strand-displacement reaction was carried out by adding Phi29 DNA polymerases (Enzymatics, Beverly, Calif.) and 200 uM of dNTPs to the ligation reaction followed by incubation at 30° C. for 15 minutes. Afterwards, Zymoclean DNA Recovery Kit (Zymo, Irvine, Calif.) was used to purify the resulting library ligated to the adaptors and to remove unligated adaptors. Purified DNA libraries containing the adaptors will be identified as $S_0$ (Sample 0).

Library amplification: $S_0$ libraries were PCR amplified using the pair of oligonucleotides Primer-fw/Primer-rv under two different conditions: a) Regular PCR: Kapa Hifi Hotstart (KAPA Biosystems. Willmington, Mass.) was used to amplify the library sample that will be targeted in the digestion process. The PCR product was gel extracted using Zymoclean Gel DNA Recovery Kit (Zymo, Irvine, Calif.). The expected band has an estimated size of 368 bp (59 bp Promoter adaptor+aprox. 200 bp genomic/plasmid DNA+ 109 bp Scaffold adaptor). As the library had undergone 20 PCR amplification cycles it was identified as $S_{20}$, b) Uracil-incorporating PCR: In order to reduce the carry-over of DNA from in vitro transcription, Luna Universal qPCR Master Mix (NEB. Ipswich, Mass.) was also used to amplify $S_0$. This PCR master mix contains a blend of dTTP and dUTP so that a certain percentage of thymidine bases in the PCR product are substituted by Uracil. This PCR product was purified in the same fashion as $S_{20}$, and identified as $S_{20}$-U. The use of $S_{20}$-U as template for IVT would allow its complete removal from the resulting transcript RNAs through the application of the USER enzyme mix.

In Vitro Transcription (IVT) and RNA purification: $S_{20}$-U was used as template to generate the stgRNA necessary for the digestion and diversity adjustment. The library is a suitable IVT template as it contains a strong T7 viral promoter included in the Promoter adaptor (see above). The transcript starts at T7 transcription start site (position 55 of the Promoter adaptor) and it ends by run off after transcribing the plasmid/genome fragment and the stgRNA Scaffold adaptor. IVT was performed using T7 RNA polymerase (Enzymatics, Beverly, Calif.) in standard conditions with all nucleotide triphosphates (ATP. GTP, CTP, UTP) for 8 hours at 37° C. In order to eliminate the DNA template, which could otherwise amplify in later PCR steps, from this RNA mix, the IVT product was first treated for 40 minutes at 37° C. with a mix of DNase I, UDG (Uracil DNA Glycosylase) and Endo VIII (Endonuclease VIII) (Enzymatics, Beverly, Calif.). The sample is then purified with a Qiagen miRNeasy Mini Kit (Qiagen, Hilden, Germany) including an extra in-column DNase digestion using Qiagen RNase-free DNase Set (Qiagen, Hilden, Germany). The purified RNA is eluted in DEPC water. A second UDG treatment was performed for 30 minutes at 37° C. on the purified RNA. For this second UDG treatment, Antarctic Thermolabile UDG (NEB, Ipswich, Mass.) was used. This UDG enzyme is susceptible to thermal inactivation and was inactivated for 5 min at 50° C. This RNA sample after inactivation treatment was identified as stgRNA-$S_{20}$-U.

Figure 6:
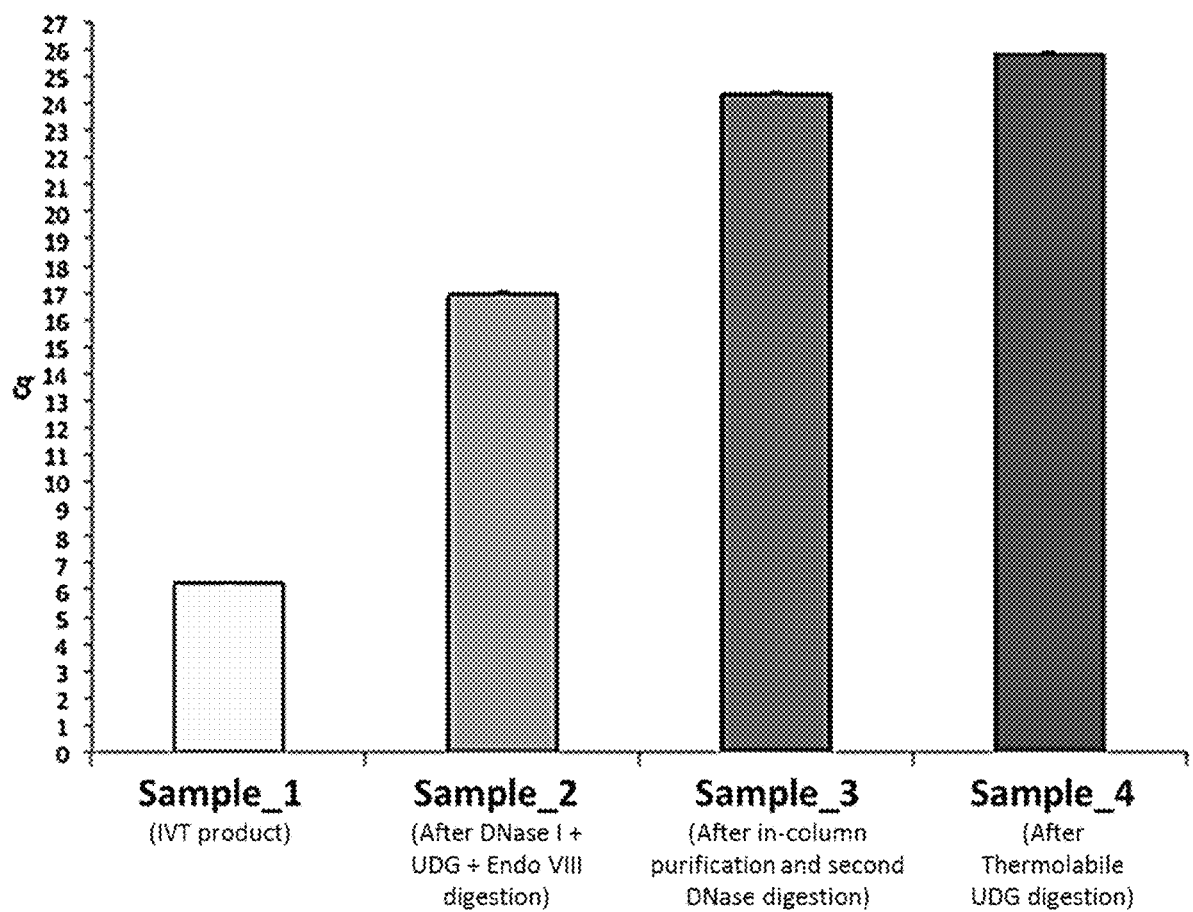
FIG. 6 is a graph of data regarding qPCR analysis of carry over DNA after different stages of RNA purification. The samples have been normalized by RNA concentration so that the proportion of DNA per RNA is comparable. Error bars represent standard deviation. The particular DNA library shown in this figure as an example corresponds to *E. coli* MG1655 genome.

To confirm that there was no significant DNA carry over from the IVT sample to later digestion steps, samples were taken at various intermediate and final stages along the purification process: Sample_1: IVT product; Sample_2: After DNase I+UDG+EndoVIII digestion: Sample_3: After in column purification (including second DNase digestion); Sample_4: After Antarctic Thermolabile UDG treatment. These RNA samples taken at different stages were quantified using Qubit RNA HS Assay Kit (Thermo-Fisher. Waltham, Mass.). They were subsequently normalized by concentration and analyzed by qPCR (KAPA SYBR Fast Universal: KAPA Biosystems, Willmington, Mass.) for the presence of carryover DNA using Primer-fw/Primer-rv. The resulting Cq values for the each sample were a proxy of the relative abundance of carry-over $S_{20}$-U DNA. FIG. 6 shows the Cq results for each sample. The results show that the combination of all DNA-removal efforts result in elimination of DNA to the level of background signal. The Cq value of the Sample_4, taken after the last treatment, shared almost the same value as a control without DNA (Cq=27).

Cas9 treatment was performed as follows.

Cas9 Footprinting and Digestion: The natural gRNA: Cas9 complex recognizes a 20 b protospacer followed by the gRNA scaffold. In the present disclosure, long stgRNA are generated that contain approximately 200 bases of RNA fused to the stgRNA scaffold. Moreover, the stgRNA scaffold is transcribed with the sequencing primer Primer-rv at its 3' side. As a result, the transcribed stgRNA has extra sequence both upstream and downstream of stgRNA. A Cas9 footprinting method as described in FIG. 7 was used to shorten the transcribed stgRNA keeping intact the protospacer and scaffold regions. The enzymes used for the footprinting are Apyrase and XRN-1 (NEB, Ipswich, Mass.). These two enzymes shorten the 5' end of the stgRNA, which carries the longest overhang compared to a canonical stgRNA. Apyrase catalyses the conversion of 5' triphosphorylated RNA to 5' monophosphorylated RNA by sequential removal of γ and β phosphates. This dephosphorylation transforms the 5' of the stgRNA into a suitable substrate for XRN-1, a highly processive 5'→3' exoribonuclease requiring a 5' monophosphate as starting point. Exo-T (Exonuclease T; NEB. Ipswich, Mass.), carries out the Cas9 footprinting from the 3' end of the stgRNA by degrading the Primer-rv overhang due to its highly processive 3'→5' exoribonuclease activity.

Footprinting and digestion were carried out in a 15 ul reaction volume. Firstly, target DNA $S_{20}$ (ranging between 0.3 nM and 0.03 nM), stgRNA-$S_{20}$-U for Cas9 nuclease (in 10 to 100 fold molar excess of the DNA) and 60 nM Cas9 nuclease from *S. pyogenes* (NEB, Ipswich, Mass.) were mixed in the reaction buffer. The reaction was then incubated for 15 minutes at 37° C., allowing for stgRNA:Cas9 complexes to be formed. After this incubation, RNA Footprinting enzymes (0.5 U Apyrase; 1 U XRN-1; 1 U Exo-T) were added to the mix, which was subsequently incubated for 8 hours at 37° C.

For each footprinting in a digestion reaction, a negative control counterpart was also assembled that contained all the components of the positive reaction except for the stgRNA library. These negative control (Neg) libraries will be compared with digested (Dig) libraries.

Verification of the digestion through electrophoresis analysis was carried out as follows. Control reactions containing 0.3 nM target DNA allowed the visualization of library digestion by Cas9 after electrophoretic separation on 10% TBE-polyacrylamide gels (Invitrogen, Carlsbad, Calif.) under non-denaturing conditions. Before loading on a gel, samples were treated with RNase (RiboShredder RNase blend; Epicentre, Madison, Wis.) for 2 hours at 37° C. followed by Proteinase K (NEB. Ipswich, Mass.) for 15 minutes at 50° C. to remove all protein and RNA components. Samples were loaded into the 10% TBE-PAGE using Gel Loading Dye Purple 6× without SDS (NEB, Ipswich, Mass.) and run at 180V for 70 minutes. After the run, the gel was stained using SYBR Gold Nucleic Acid Stain as shown in FIG. 8A and FIG. 8B. These in vitro analyses showed successful partial digestion of plasmid (see FIG. 8A) and genomic libraries (see FIG. 8B) DNA libraries using Cas9 nuclease and stgRNA library derived from the same samples.

Sequencing: The E. coli genomic DNA library obtained above and its negative (non stgRNA normalized) counterpart were amplified with Illumina sequencing adaptors and primers with a unique index to obtain sequencing. The indexed libraries were combined after purification and sequenced on a MiSeq platform with a 300V2 kit with 200 bp forward reads. For the positive stgRNA normalized sample (Dig) 1,767,278 reads were obtained. For its negative counterpart (Neg1) that was amplified without normalization 1,621,505 reads were obtained. Finally, 1,783,679 reads were obtained for a replicated negative sample (Neg2).

Figure 9A:
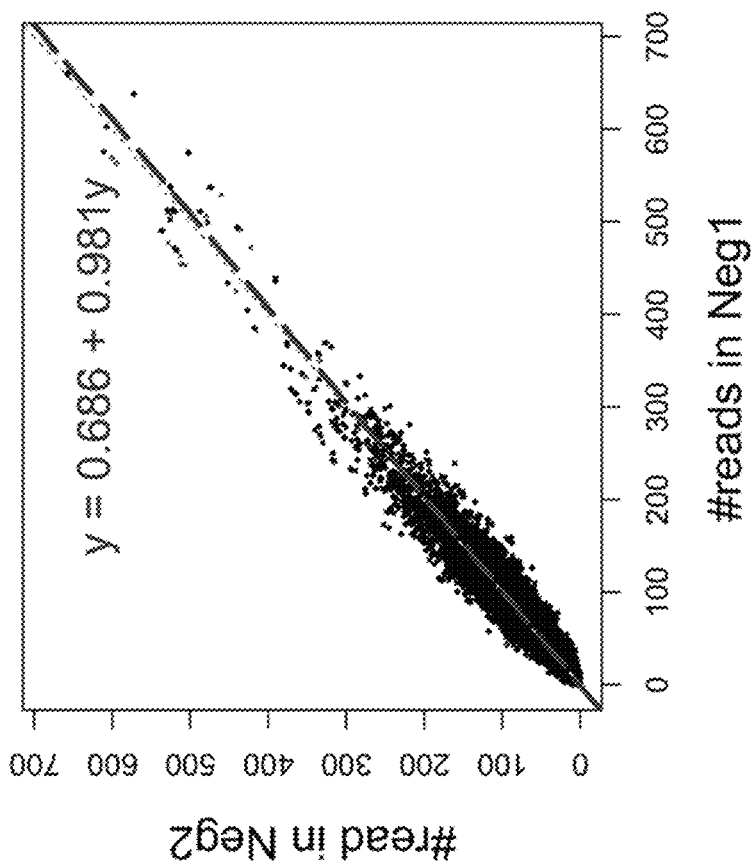
FIG. 9A-B are directed to plots showing the coverage of *E. coli* genome in the non-adjusted (Neg1) sample and the stgRNA PCR-bias adjusted (Dig) sample, showing reduction of highly frequent samples and increase in low frequency samples in Dig compared to Neg1. The grey dotted line represents the expected trendline if the treatment had no effect on the Dig library. The dashed red line is the observed trendline, demonstrating significant difference in the direction of bias removal in the Dig library. The X and Y axis are in units of normalized observed coverage counts. Each spot on the plot represents a base in the *E. coli* genome with coverage bigger than 0 in either sample. The blue arrow on the right in FIG. 9A shows the highly covered regions from Neg1 whose coverage has been significantly reduced in Dig. The green arrow on the left in FIG. 9A shows the regions with low coverage in Neg1 whose coverage has improved, though slightly per region, drastically for their total sum, in Dig.
Figure 9B:
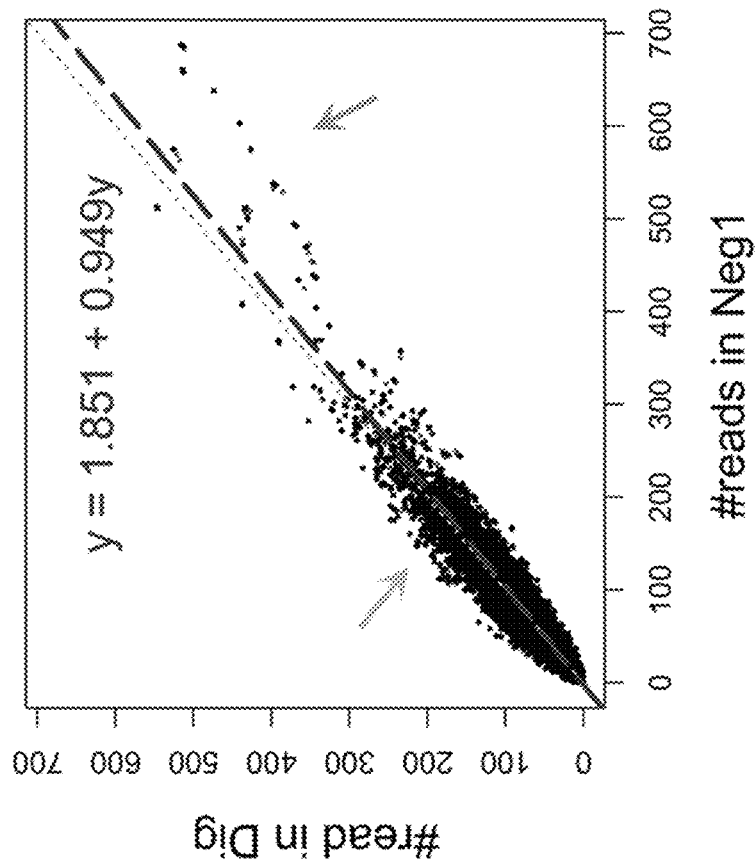

Analysis: Each dataset was assembled to the reference genome for E. coli MG1655 using the Geneious software suite. The reference genome is circular and 4,641,652 bp in length. The amount of genomic coverage in each of the three samples (Dig, Neg1. Neg2) was calculated as the number of reads that cover each of the 4,641.652 positions in the genome. The coverage counts were normalized by total read count for each sample. For two pairs of samples (Dig-Neg1 and Neg2-Neg1) the coverage of all covered positions in the genome was plotted and a linear trendline was calculated. The results show that only in the partially digested Cas9-stgRNA sample, the distribution for amplicons has been altered (see FIG. 9A). Specifically, the trendline indicates that the slope of the plot of 0.949 is significantly smaller than 1 while its intercept of 1.851 is significantly larger than 0, indicating that in the Dig sample there is a higher representation of the less abundant constructs in Neg1 and a lower representation of the highly abundant constructs in Neg1. As a result, the FIG. 9A plot shows genomic regions with very high coverage far further below the trendline whereas points with low coverage fall higher than the trendline. These adjustments in amplicon frequency cannot be observed in FIG. 9B which plots two negative samples versus one another, where the slope of the trendline is close to 1 and its intercept is close to 0.

Accordingly, this Example shows in vitro digestion of library DNA with stgRNAs derived from the library itself or its parent library. It also shows reduction of PCR bias in complex libraries of E. coli genomic DNA. While limited digestion by Cas9-stgRNA was applied, more extensive digestion can lead to further bias reduction in the PCR library.

What is claimed is:

1. A method of processing a collection of nucleic acid sequences comprising
   connecting an adaptor to one or more members of the nucleic acid sequences in the collection to create a processed nucleic acid template library, wherein the adaptor includes a first DNA sequence encoding a protospacer adjacent motif (PAM) sequence, a tracr mate sequence and a tracrRNA sequence, forming a sequence encoding a guide RNA scaffold sequence
   amplifying members of the processed nucleic acid template library in a polymerase chain reaction (PCR), wherein a thermophilic Cas nuclease and a thermophilic RNA polymerase are added to the PCR reaction, and where in each amplification cycle, the RNA polymerase transcribes a guide RNA from members of the nucleic acid template library and Cas nuclease forms a colocalization complex with transcribed guide RNAs and target amplicons corresponding to guide RNAs, and wherein the Cas nuclease cuts the target amplicon to reduce amplification bias in the library of DNA amplicons to create an adjusted amplified library.

2. The method of claim 1 wherein the first DNA sequence further encodes a tracrRNA sequence connected to the tracr mate sequence.

3. The method of claim 1 wherein the first DNA sequence further encodes a tracrRNA sequence connected to the tracr mate sequence by a linker sequence.

4. The method of claim 1 wherein the PAM sequence is immediately adjacent to the tracr mate sequence.

5. The method of claim 1 wherein the PAM sequence is located relative to the tracr mate sequence such that expression of the first DNA sequence results in a self-targeting or homing guide RNA.

6. The method of claim 1 wherein the PAM sequence is inside the tracr mate sequence.

7. The method of claim 1 wherein the guide RNA scaffold sequence is a CRISPR guide RNA scaffold sequence.

8. The method of claim 1 wherein the guide RNA scaffold sequence is a modified guide RNA scaffold sequence including the PAM sequence such that it is capable of self-targeting or homing activity.

9. The method of claim 1 further including connecting a promoter to the one or more members of the nucleic acid sequences in the collection.

10. The method of claim 1 wherein each member of the processed nucleic acid template library includes a barcode unique to that member.

11. The method of claim 1 wherein the collection of nucleic acid sequences includes DNA sequences.

12. The method of claim 1 wherein the collection of nucleic acid sequences includes double stranded DNA sequences.

13. The method of claim 1 wherein the collection of nucleic acid sequences includes DNA sequences selected from the group consisting of chromosomal DNA, mitochondrial DNA, viral DNA or metagenomics DNA sequences.

14. The method of claim 1 wherein the collection of nucleic acid sequences includes synthetic DNA sequences.

15. The method of claim 1 wherein the first DNA sequence is connected to the one or more member of the nucleic acid sequences in the collection by ligation, transposition or PCR.

16. The method of claim 1 wherein the nucleic acid sequences in the collection have unknown nucleic acid sequences.

17. The method of claim 1 wherein the collection of nucleic acid sequences includes RNA sequences.

18. The method of claim 1 wherein the collection of nucleic acid sequences includes DNA sequences generated by reverse transcription of RNA sequences.

19. The method of claim 1 wherein the transcribed guide RNA includes a spacer sequence complementary to a protospacer sequence of the processed nucleic acid template library.

20. The method of claim 1 wherein the RNA polymerase is T7 RNA polymerase, *E. coli* RNA polymerase or SP6 RNA polymerase.

21. The method of claim 1 further comprising connecting a promoter to each member of the nucleic acid sequence in the collection and amplifying the processed nucleic acid template library to create an amplicon library.

22. The method of claim 21 wherein members of the processed nucleic acid template library are selected to produce a subset library before amplification to produce the amplicon library.

23. The method of claim 1 further comprising
(a) connecting a promoter to each member of the nucleic acid sequence in the collection and amplifying the processed nucleic acid template library to create an amplicon library, and
(b) creating a guide RNA library from corresponding members of the amplicon library wherein each member of the guide RNA library includes a spacer sequence complementary to a protospacer sequence of the corresponding member of the amplicon library.

24. The method of claim 23 wherein each member of the guide RNA library correlates in number with its corresponding member of the amplicon library.

25. The method of claim 1 wherein the Cas nuclease is a Cas9 nuclease, a Cas9 nuclease.

26. The method of claim 1 wherein the Cas nuclease is a spCas9 nuclease.

27. The method of claim 1 wherein the Cas nuclease is *S. pyogenes* Cas9, *S. thermophilis* Cas9, *N. meningitidis* Cas9, *T. denticola* Cas9, or *S. aureus* Cas9.

28. The method of claim 1 wherein the Cas nuclease is a Cpf1 nuclease, a Cpf1 nuclease.

29. The method of claim 1 wherein the one or more members of the amplicon library are cut to remove the one or more members of the amplicon library from the amplicon library.

30. The method of claim 1 wherein the one or more members of the amplicon library are cut to enrich amplicons in the amplicon library.

31. The method of claim 1 wherein the one or more members of the processed nucleic acid template library are cut to enrich nucleic acids in the processed nucleic acid template library.

32. A method of reducing amplification bias in a library of DNA amplicons comprising
connecting a promoter sequence and a first DNA sequence encoding a PAM sequence, a tracr mate sequence and a tracrRNA sequence to each member of a DNA library to create a processed DNA template library, wherein a portion of the member of the DNA library, the PAM sequence, the tracr mate sequence and the tracrRNA sequence form a self-targeting or homing guide RNA template sequence, and
amplifying members of the processed DNA template library in a polymerase chain reaction (PCR), wherein a thermophilic Cas nuclease and a thermophilic RNA polymerase are added to the PCR reaction, and where in each amplification cycle, the RNA polymerase transcribes a guide RNA from members of the DNA template library and Cas nuclease forms a colocalization complex with transcribed guide RNAs and target amplicons corresponding to guide RNAs, and wherein the Cas nuclease cuts the target amplicon to reduce amplification bias in the library of DNA amplicons to create an adjusted amplified library.

* * * * *

SEQUENCE LISTING

```
<160> NUMBER OF SEQ ID NOS: 9

<210> SEQ ID NO 1
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other
<220> FEATURE:
<221> NAME/KEY: misc_feature
<222> LOCATION: (1)..(20)
<223> OTHER INFORMATION: This region may encompass 8-20 nucleotides,
      wherein some may be absent

<400> SEQUENCE: 1
nnnnnnnnnn nnnnnnnnnn gttttagagc tagaaatagc aagttaaaat aaggctagtc      60
cgttatcaac ttgaaaaagt ggcaccgagt cggtgctttt ttt                       103

<210> SEQ ID NO 2
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
acactctttc cctacacgac gctcttccga tctaattaat acgactcact atagggaga      59
```

-continued

```
<210> SEQ ID NO 3
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gggttagagc tagaaatagc aagttaacct aaggctagtc cgttatcaac ttgaaaaagt        60
ggcaccgagt cggtgctaga tcggaagagc acacgtctga actccagtc                   109

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
acgacgctct tccgatctaa ttaatacgac tcactatagg gaga                         44

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tctccctata gtgagtcgta ttaattagat cggaagag                                38

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gggttagagc tagaaatagc aagttaacct aaggctag                                38

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
taacggacta gccttaggtt aacttgctat ttctagctct aaccc                        45

<210> SEQ ID NO 8
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
```

```
<400> SEQUENCE: 8
nnnnnnnnnn nnnnnnnnnn guuuuagagc uagaaauagc aaguuaaaau aaggcuaguc      60
cguuaucaac uugaaaaagu ggcaccgagu cggugc                                96

<210> SEQ ID NO 9
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 9
nnnnnnnnnn nnnnnnnnnn ggguuagagc uagaaauagc aaguuaaccu aaggcuaguc      60
cguuaucaac uugaaaaagu ggcaccgagu cggugc                                96
```